US009458472B2

(12) United States Patent
Weiss et al.

(10) Patent No.: US 9,458,472 B2
(45) Date of Patent: Oct. 4, 2016

(54) DETECTION AND DESTRUCTION OF CANCER CELLS USING PROGRAMMED GENETIC VECTORS

(75) Inventors: Ron Weiss, Newton, MA (US); Priscilla E. M. Purnick, West Windsor, NJ (US); Caroline DeHart, Fort Lauderdale, FL (US); Jon Monk, New York, NY (US); Aparna Swaminathan, Orefield, PA (US)

(73) Assignee: Massachusetts Institute of Technology, Cambridge, MA (US)

( * ) Notice: Subject to any disclaimer, the term of this patent is extended or adjusted under 35 U.S.C. 154(b) by 178 days.

(21) Appl. No.: 12/587,994

(22) Filed: Oct. 15, 2009

(65) Prior Publication Data

US 2011/0237652 A1 Sep. 29, 2011

Related U.S. Application Data

(60) Provisional application No. 61/105,706, filed on Oct. 15, 2008.

(51) Int. Cl.
| | |
|---|---|
| *A61K 48/00* | (2006.01) |
| *A61P 35/00* | (2006.01) |
| *C12N 15/86* | (2006.01) |
| *C12N 15/63* | (2006.01) |
| *A61K 35/13* | (2015.01) |
| *C12N 15/113* | (2010.01) |

(52) U.S. Cl.
CPC ........... *C12N 15/86* (2013.01); *A61K 48/0058* (2013.01); *C12N 15/63* (2013.01); *A61K 35/13* (2013.01); *C12N 15/113* (2013.01); *C12N 2310/14* (2013.01); *C12N 2740/15043* (2013.01); *C12N 2840/005* (2013.01); *C12N 2840/007* (2013.01); *C12N 2840/102* (2013.01); *C12N 2840/85* (2013.01); *C12N 2999/007* (2013.01)

(58) Field of Classification Search
USPC ................. 435/6, 6.1, 6.11, 6.14, 6.19, 91.1, 435/91.31, 375, 455, 320.1; 514/1, 2, 44; 530/300, 350; 536/23.1, 23.5, 24.5; 424/9.1
See application file for complete search history.

(56) References Cited

U.S. PATENT DOCUMENTS

| | | | |
|---|---|---|---|
| 4,683,195 A | 7/1987 | Mullis et al. | 435/6.11 |
| 4,683,202 A | 7/1987 | Mullis | 435/91.2 |
| 4,965,188 A | 10/1990 | Mullis et al. | 435/6.12 |
| 6,774,222 B1 | 8/2004 | Schneider et al. | 536/23.1 |
| 8,034,598 B2 * | 10/2011 | Miller | 435/199 |
| 2009/0004668 A1 * | 1/2009 | Chen et al. | 435/6 |
| 2009/0215992 A1 * | 8/2009 | Wu et al. | 530/387.3 |
| 2011/0183336 A1 * | 7/2011 | Gray et al. | 435/6.12 |

FOREIGN PATENT DOCUMENTS

WO     WO 02/44321     *     6/2002

OTHER PUBLICATIONS

Lacroix et al., Mole. Cell Endocrinol., vol. 219, pp. 1-7 (2004).*
Tanaka et al, Clin. Cancer Res., vol. 6, pp. 127-134 (2000).*
Chinnaiyan et al, Proc. Natl. Acad. Sci. USA, vol. 97, pp. 1754-1759 (2000).*
Doench et al., Genes & Development, vol. 18, No. 5, pp. 504-511 (2004).*
Paroo, Z et al., Trends in Biotechnology, vol. 22, No. 8 (2004).*
Holen et al., Nucleic Acids Res., vol. 30, No. 8, pp. 1757-1766 (2002).*
Abba, M. et al. (2004) Transcriptomic changes in human breast cancer progression as determined by serial analysis of gene expression, *Breast Cancer Res* 6(5), R499-R513.
Adar, R. et al. (2004) Stochastic computing with biomolecular automata, *Proceedings of the National Academy of Sciences of the United States of America 101*(27), 9960-9965.
Anderson, M. L. M. and Young, B. D. (1985) Quantitative Filter Hybridization, in *Nucleic Acid Hybridisation: A Practical Approach* (Hames, B. D., and Higgins, S. J., Eds.), pp. 73-111, Oxford University Press, USA.
Basu, S. et al. (2005) A synthetic multicellular system for programmed pattern formation, *Nature 434*(7037), 1130-1134.
Basu, S. et al. (2003) Engineering signaling processing in cells: Towards molecular concentration band detection, *Natural Computing 2*, 463-478.
Basu, S. et al. (2004) Spatiotemporal control of gene expression with pulse-generating networks, *Proceedings of the National Academy of Sciences of the United States of America 101*(17), 6355-6360.

(Continued)

*Primary Examiner* — Jane Zara
(74) *Attorney, Agent, or Firm* — Medlin & Carroll, LLP

(57) ABSTRACT

In its various embodiments, the invention provides, first, a composition comprising a vector for transfecting a cell. The vector comprises a first nucleic acid encoding an antisense agent having thereon an RNA interference target for a transcript of a gene endogenous to the cell. The vector further comprises a second nucleic acid that encodes a cell-killing agent. The second nucleic acid further comprises a sequence of nucleotides transcribable into a non-coding region of a transcript of the second nucleic acid, such that the non-coding region becomes an RNA interference target for the antisense agent. In the transfected cell, the vector operates to interfere with the expression of the cell-killing agent unless and until the vector senses certain endogenous gene signals, whereupon it releases the cell-killing agent. Second, the invention provides a method of treating a disease in a patient by killing cells responsible for the disease, the method comprising administering the vector to the patient until the disease, or a symptom thereof, is ameliorated.

2 Claims, 7 Drawing Sheets

(56) References Cited

OTHER PUBLICATIONS

Bayer, T. S. and Smolke, C. D. (2005) Programmable ligand-controlled riboregulators of eukaryotic gene expression, *Nature Biotechnology* 23(3), 337-343.

Benenson, Y. et al. (2004) An autonomous molecular computer for logical control of gene expression, *Nature* 429(6990), 423-429.

Braun, D. et al. (2005) Parameter estimation for two synthetic gene networks: a case study, in *Acoustics, Speech, and Signal Processing, 2005. Proceedings. (ICASSP '05). IEEE International Conference on*, pp. v/769-v/772 vol. 765.

Brenner, K. et al. (2007) Engineered bidirectional communication mediates a consensus in a microbial biofilm consortium, *Proceedings of the National Academy of Sciences* 104(44), 17300-17304.

Carthew, R. W. (2001) Gene silencing by double-stranded RNA, *Current Opinion in Cell Biology* 13(2), 244-248.

Chen, M.-T. and Weiss, R. (2005) Artificial cell-cell communication in yeast *Saccharomyces cerevisiae* using signaling elements from Arabidopsis thaliana, *Nature Biotechnology* 23(12), 1551-1555.

Coller, H. A. et al. (2006) A New Description of Cellular Quiescence, *PLoS Biol* 4(3), e83.

Coura, R. and Nardi, N. (2007) The state of the art of adeno-associated virus-based vectors in gene therapy, *Virology Journal* 4(1), 99.

Feng, X.-j. et al. (2004) Optimizing Genetic Circuits by Global Sensitivity Analysis, *Biophysical Journal* 87(4), 2195-2202.

Gerchman, Y. and Weiss, R. (2004) Teaching bacteria a new language, *Proceedings of the National Academy of Sciences of the United States of America* 101(8), 2221-2222.

Germain, M. et al. (2008) MCL-1 Inhibits BAX in the Absence of MCL-1/BAX Interaction, *Journal of Biological Chemistry* 283(10), 6384-6392.

Goldstein, J. C. et al. (2000) The coordinate release of cytochrome c during apoptosis is rapid, complete and kinetically invariant, *Nature Cell Biology* 2(3), 156-162.

Griffiths-Jones, S. (2004) The microRNA Registry, *Nucleic Acids Research* 32(suppl 1), D109-D111.

Hooshangi, S. et al. (2005) Ultrasensitivity and noise propagation in a synthetic transcriptional cascade, *Proceedings of the National Academy of Sciences of the United States of America* 102(10), 3581-3586.

Hooshangi, S. and Weiss, R. (2006) The effect of negative feedback on noise propagation in transcriptional gene networks, *Chaos* 16(2), 026108.

Hsu, A. et al. (2005) Dynamic control in a coordinated multicellular maze solving system, *American Controls Conference* 6(4399-4404).

Isaacs, F. J. et al. (2004) Engineered riboregulators enable post-transcriptional control of gene expression, *Nature Biotechnology* 22(7), 841-847.

Jiang, P. et al. (2007) RFRCDB-siRNA: Improved design of siRNAs by random forest regression model coupled with database searching, *Computer methods and programs in biomedicine* 87(3), 230-238.

Karig, D. and Weiss, R. (2005) Signal-amplifying genetic circuit enables in vivo observation of weak promoter activation in the Rh1 quorum sensing system, *Biotechnology and Bioengineering* 89(6), 709-718.

Kobayashi, T. et al. (1998) Overexpression of Bax gene sensitizes K562 erythroleukemia cells to apoptosis induced by selective chemotherapeutic agents, *Oncogene* 16(12), 1587-1591.

Kouros-Mehr, H. et al. (2008) GATA-3 Links Tumor Differentiation and Dissemination in a Luminal Breast Cancer Model, *Cancer Cell* 13(2), 141-152.

Kubli, D. A. et al. (2007) Bnip3 mediates mitochondrial dysfunction and cell death through Bax and Bak, *Biochemical Journal* 405(3), 407-415.

Leavitt, A. D. et al. (1996) Human immunodeficiency virus type 1 integrase mutants retain in vitro integrase activity yet fail to integrate viral DNA efficiently during infection, *Journal of Virology* 70(2), 721-728.

Lloyd, A. G. et al. (2007) Characterization of HIV-1 integrase N-terminal mutant viruses, *Virology* 360(1), 129-135.

McDaniel, R. and Weiss, R. (2005) Advances in synthetic biology: on the path from prototypes to applications, *Current Opinion in Biotechnology* 16(4), 476-483.

Needleman, S. B. and Wunsch, C. D. (1970) A general method applicable to the search for similarities in the amino acid sequence of two proteins, *J. Mol. Biol.* 48(3), 443-453.

Nugoli, M. et al. (2003) Genetic variability in MCF-7 sublines: evidence of rapid genomic and RNA expression profile modifications, *BMC Cancer* 3(1), 13.

Park, W. et al. (2008) "Cancer gene therapy using adeno-associated virus vectors," *Frontiers in Bioscience* 13, 2653-2659.

Patzel, V. (2007) In silico selection of active siRNA, *Drug Discovery Today* 12(3-4), 139-148.

Pearson, W. R. and Lipman, D. J. (1988) Improved tools for biological sequence comparison, *Proceedings of the National Academy of Sciences* 85(8), 2444-2448.

Philippe, S. et al. (2006) Lentiviral vectors with a defective integrase allow efficient and sustained transgene expression in vitro and in vivo, *Proceedings of the National Academy of Sciences* 103(47), 17684-17689.

Rinaudo, K. et al. (2007) a universal RNAi-based logic evaluator that operates in mammalian cells, *Nature Biotechnology* 25(7), 795-801.

Saelens, X. et al. (2004) Toxic proteins released from mitochondria in cell death, *Oncogene* 23(16), 2861-2874.

Sambrook, J. et al. (1989) in *Molecular Cloning: A Laboratory Manual* (Sambrook, J., Fritsch, E. F., and Maniatis, T., Eds.) 2nd ed., pp. 9.31-9.58, Cold Spring Harbor Laboratory Press, New York.

Sambrook, J. et al. (1989) in *Molecular Cloning: A Laboratory Manual* (Sambrook, J., Fritsch, E. F., and Maniatis, T., Eds.) 2nd ed., pp. 7.39-37.52, Cold Spring Harbor Laboratory Press, New York.

Smith, T. F. and Waterman, M. S. (1981) Comparison of biosequences, *Advances in Applied Mathematics* 2(4), 482-489.

Sumimoto, H. et al. (2006) Effective inhibition of cell growth and invasion of melanoma by combined suppression of BRAF (V599E) and Skp2 with lentiviral RNAi, *International Journal of Cancer* 118(2), 472-476.

Sumimoto, H. and Kawakami, Y. (2007) "Lentiviral vector-mediated RNAi and its use for cancer research," *Future Oncology* 3(6), 655-664.

Thiberge et al. (2003) "Quantum-dot-based measurement of gene expression."

Ui-Tei, K. et al. (2004) Guidelines for the selection of highly effective siRNA sequences for mammalian and chick RNA interference, *Nucleic Acids Research* 32(3), 936-948.

Upton, J. P. et al. (2007) The N-terminal conformation of Bax regulates cell commitment to apoptosis, *Cell Death Differ* 14(5), 932-942.

Weiss, R. et al. (1999) Toward in-vivo digital circuits, in *Dimacs Workshop on Evolution as Computation*, Princeton, N.J.

Weiss, R. and Jr., T. F. K. (2000) Engineered communications for microbial robotics, in *DNA6: Sixth International Workshop on DNA-Based Computers, DNA2000*, pp. 1-16, Springer-Verlag, Leiden, The Netherlands.

Weiss, R. (2001) Cellular Computation and Communications using Engineered Genetic Regulatory Networks, PhD Thesis, Massachusetts Institute of Technology.

Weiss, R. and Basu, S. (2002) The device physics of cellular logic gates, in *NSC-1: The First Workshop of Non-Silicon Computing*, pp. 54-61, Boston, Mass.

Weiss, R. (2003) "Challenges and Opportunities in Programming Living Cells," *The Bridge*, 39-46.

Weiss, R. et al. (2003) Genetic circuit building blocks for cellular computation, communications, and signal processing, *Natural Computing* 2(1), 47-84.

Weiss, R. et al. (2004) Genetic process engineering, in *Cellular Computing* (Amos, M., Ed.), Oxford University Press.

Weiss R., "Synthetic Biology", DAC Jun. 4-8, 2007.

(56) References Cited

OTHER PUBLICATIONS

Win, M. N. and Smolke, C. D. (2007) A modular and extensible RNA-based gene-regulatory platform for engineering cellular function, *Proceedings of the National Academy of Sciences* 104(36), 14283-14288.

Wiznerowicz, M. and Trono, D. (2003) Conditional Suppression of Cellular Genes: Lentivirus Vector-Mediated Drug-Inducible RNA Interference, *Journal of Virology* 77(16), 8957-8951.

Yáñez-Muñoz, R. J. et al. (2006) Effective gene therapy with nonintegrating lentiviral vectors, *Nature Medicine* 12(3), 348-353.

Yokobayashi et al. (2003) Evolutionary design of genetic circuits and cell-cell communication, *Advances in Complex Systems* 6(1), 37-45.

Yokobayashi, Y. et al. (2002) Directed evolution of a genetic circuit, *Proceedings of the National Academy of Sciences* 99(26), 16587-16591.

You, L. et al. (2004) Programmed population control by cell-cell communication and regulated killing, *Nature* 428(6985), 868-871.

Xie, Z. et al., Multi-input RNAi-based logic circuit for identification of specific cancer cells. *Science,* Sep. 2, 2011;333(6047):1307-11.

Dejori, M. and Stetter, M. (2004) "Identifying interventional and pathogenic mechanisms by generative inverse modeling of gene expression profiles," *Journal of Computational Biology* 11(6), 1135-1148.

Patzel, "In silico selection of active siRNA." Drug Discovery Today, 12:139-148 (2007).

GenBank accession No. AY497006.1.

GenBank accession No. NM_000909.5.

GenBank accession No. NM_003225.2.

"Advances in Understanding Genetic Changes in Cancer: Impact on Diagnosis and Treatment Decisions in the 1990s," Publisher: National Academies Press, Washington, D.C., 1992.

La Cour et al.. (2008) "The apoptosis linked gene ALG-2 is dysregulated in tumors of various origin and contributes to cancer cell viability," Molecular Oncology 1:431-439.

Ebert et al.. "MicroRNA sponges: competitive inhibitors of small RNAs in mammalian cells," Nature Methods 4, 721-726 (2007).

GenBank accession No. NM_138764.4.

GenBank accession No. NM_138761.3.

GenBank accession No. NM_004324.3.

GenBank accession No. NM_138763.3.

GenBank accession No. U16811.1.

Niu et al.. "Gene Therapy with Dominant-negative Stat3 Suppresses Growth of the Murine Melanoma B16 Tumor in Vivo," Cancer Research 59:5059-5063 (1999).

\* cited by examiner

GATA3mut02 siRNA siRNA BINDS          C-G-A-G-T-C-G-C-T-G-A-A-G-A-G-G-T-T-C-T-G     SEQ ID NO: 1
ENDOGENOUS           | | | | | | | | | | | | | | | | | | | |
GATA3 SEQUENCE       T-C-T-C-A-G-C-G-C-C-T-T-C-T-C-C-A-A-G-A-C     SEQ ID NO: 2

U - C
                     SEQ ID NO: 3                        U /     \
                                                        /         A
                     C-G-A-G-T-C-G-C-T-G-A-A-G-A-G-G-T-T-C-T-G  C   \
GATA3 ahRNA          | | | | | | | | | | | | | | | | | | | |        A
                     G-C-T-C-A-G-C-G-A-C-T-T-C-T-C-C-A-A-G-A-C  G  /
                                                             \    G
                                                              A  /
                                                               G-A siRNA BINDS          C-G-A-G-T-C-G-C-T-G-A-A-G-A-G-G-T-T-C-T-G     SEQ ID NO: 4
ENGINEERED           | | | | | | | | | | | | | | | | | | | |
GATA3 TARGET SITE    G-C-T-C-A-G-C-G-A-C-T-T-C-T-C-C-A-A-G-A-C     SEQ ID NO: 5

FIG 5A

GATA3mut11 siRNA

```
siRNA BINDS          G-T-A-A-G-T-G-G-T-A-T-A-A-T-T-G-T-C-T-G-G    SEQ ID NO: 6
ENDOGENOUS           | | | | | | | | | | | | | | | | | | | | |
GATA3 SEQUENCE       G-C-T-T-C-A-C-A-A-T-A-T-T-A-A-C-A-G-A-C-C
                     SEQ ID NO: 7
```

```
                     SEQ ID NO: 8
                     G-T-A-A-G-T-G-G-T-A-T-A-A-T-T-G-T-C-T-G-G
GATA3 ahRNA          | | | | | | | | | | | | | | | | | | | | |
                     C-A-T-T-C-A-C-C-A-T-A-T-T-A-A-C-A-G-A-C-C
```

```
siRNA BINDS          G-T-A-A-G-T-G-G-T-A-T-A-A-T-T-G-T-C-T-G-G    SEQ ID NO: 9
ENGINEERED           | | | | | | | | | | | | | | | | | | | | |
GATA3 TARGET SITE    C-A-T-T-C-A-C-C-A-T-A-T-T-A-A-C-A-G-A-C-C    SEQ ID NO: 10
```

FIG. 5B miR-611 siRNA

```
siRNA BINDS          U-G-C-G-C-G-U-C-C-G-G-U-C-U-C-U-G-G-G-U-C-C-G    SEQ ID NO: 11
ENDOGENOUS           | | | | | | | | | | | | | | | | | | | | | | |
GATA3 SEQUENCE       G-C-G-U-G-C-A-U-G-U-C-A-G-C-G-A-C-C-C-U-G-G-C    SEQ ID NO: 12
```

```
                     SEQ ID NO: 13
                     A-C-G-C-G-C-A-G-G-C-C-A-G-A-G-A-C-C-C-A-G-G
GATA3 ahRNA          | | | | | | | | | | | | | | | | | | | | | |
                     U-G-C-G-C-G-U-C-C-G-G-U-C-U-C-U-G-G-G-U-C-C
```

```
siRNA BINDS          U-G-C-G-C-G-U-C-C-G-G-U-C-U-C-U-G-G-G-U-C-C-G    SEQ ID NO: 14
ENGINEERED           | | | | | | | | | | | | | | | | | | | | | | |
GATA3 TARGET SITE    A-C-G-C-G-C-A-G-G-C-C-A-G-A-G-A-C-C-C-A-G-G-C    SEQ ID NO: 15
```

FIG. 5C

DETECTION AND DESTRUCTION OF CANCER CELLS USING PROGRAMMED GENETIC VECTORS

This application claims priority to U.S. provisional Application Ser. No. 61/105,706, filed on Oct. 15, 2008, the contents of which are herein incorporated by reference.

STATEMENT REGARDING FEDERALLY SPONSORED RESEARCH OR DEVELOPMENT

This invention was made with government support under Contract No. W81XWH-09-1-0240 awarded by the U.S. Army. The government has certain rights in the invention.

FIELD

The invention relates to the bio-engineering of cells according to principles of control systems engineering. Some embodiments of the invention find application in the field of cancer therapy.

BACKGROUND

As the mechanisms by which cells control the expression of their genetic code become better understood, concepts developed to aid the engineering of control systems in the mechanical and electrical arts are becoming increasingly applicable to the non-deterministic ("stochastic") systems that control the biochemical activities of living cells.

Control systems engineering relies heavily on permitting or preventing the passage of a signal by means of a switch. The modern computer is an elaborate system of binary ("on/off") switches (embodied in, e.g., signal diodes or their equivalent). The engineer arranges sets of switches to form logic gates (or "logic circuits") according to principles of formal logic such that one or more signals entering the gate ("inputs") contributes something (including nothing at all) to the gate's output. A gate determines its output by "evaluating" its inputs. The evaluation depends on how the gate's switches are arranged. One of the simplest gates (two switches) is an elementary "AND" gate. It requires two distinct inputs to open. If one or both inputs are absent (i.e., at least one switch is "off"), the gate remains closed. There is no output from it. A control system typically comprises a plurality of gates, variously interconnected to form a so-called logic evaluator. Control systems are typically coupled to a "controlled" system, and at least some of the inputs to the control system arise from the controlled system. Thus, one of the uses of the output of the control system is to feed back to the controlled system information about the state of the controlled system.

In the case of biomolecular control systems, the "switch," is a molecule whose chemical activity (1) exerts an influence on a (bio)chemical process, and (2) is itself affected by a (bio)chemical process. Since virtually all chemically active biomolecules in living systems mediate at least one process within a network of interacting processes, these molecular "switches" participate in an enormously complicated set of logic gates that work together to control a living system such as a cell.

Despite the complexity one confronts when viewing homeostasis in a living system as an engineered control system, elements of living systems have been isolated and used to engineer control systems. For example, Schneider et al., in "Molecular Computing Elements, Gates and Flip-Flops" U.S. Pat. No. 6,774,222, described a molecular gate based on a nucleic acid, preferably double-stranded DNA. The nucleic acid has the properties of a switch because it has more than one binding site, each specific for its own ligand. A plurality of such switches may be arranged in various configurations, enabling the construction of logic gates variously activable by one or more binding ligands.

Benenson et al., in "An Autonomous Molecular Computer for Logical Control of Gene Expression" Nature 429:423-429 (2004), described a "molecular computer" that searches for a particular set of four indicators which, when the "computer" finds them all present, a gate opens and releases a drug or a suppressor (viz., antisense ssDNA). The paper demonstrates that "stochastic computing" (wherein purely binary data, i.e., "1" or "0," are replaced by "probably 1" and "probably 0" data) can provide reliable results if the number of parallel "computations" (in this case, individual contacts between molecules) is very large. The paper demonstrates, further, that such a computer can be used programmatically to determine the output from a set of interacting molecular species in vitro. So programmed, the set performs automatically. It is an automaton.

Adar et al. ("Stochastic Computing with Biomolecular Automata" Proc. Nat'l Acad. Sci. 101:960-9965 (2004) reported on a similar computing automaton. The computer accepts "data" encoded in a DNA molecule and processes the data with one or more enzymes that digest DNA. The enzymes are analogous to computer hardware. Whether or not the "hardware" actually digests the input DNA, and in what way, depends on the specific composition of a mixture of molecules that affect the enzymes. Such mixtures, in effect, "program" the hardware. They are therefore analogous to the software that modern computers employ.

Whereas Benenson et al. relied on restriction enzymes (e.g., Fok1) to manipulate inputted DNA, Win et al., in "A Modular and Extensible RNA-Based Gene-Regulatory Platform for Engineering Cellular Function" PNAS 104(36): 14283-14288 (2007), employed a hammerhead ribozyme (catalytic RNA) with "riboswitch" properties. The construct comprises (1) an aptamer specific for a pre-determined ligand (e.g., theophylline) and (2) a ribozyme coupled to the aptamer in such a way that when the aptamer binds ("senses") the ligand, the ribozyme domain is actuated. Win et al. focused on attaining external control over gene expression. They did not suggest a means of introducing into a cell a system that would internally control gene expression.

Bayer et al., "Programmable Ligand-Controlled Riboregulators of Eukaryotic Gene Expression" Nat. Biotechnol. 23:337-343 (2005) described an RNA construct for controlling gene expression, the construct comprising an antisense domain and a ligand-sensitive aptamer domain. Aptamer-ligand binding changes the conformation of the construct. The resultant change may enable the antisense domain to interact with a target mRNA in a way that interferes with translation. The experiments described in the reference put the focus on introducing a switching mechanism into a cell in order to achieve external control over expression.

Another approach to suppressing gene expression is exemplified by Isaacs et al. in "Engineered Riboregulators Enable Post-Transcriptional Control of Gene Expression" Nat. Biotechnol. 22:841-847 (2004). Essentially, the technology sequesters the ribosome binding site on messenger RNA by "hiding" it in a fold or loop on messenger RNA. The technique requires engineering a mutation into the DNA that encodes the messenger RNA the engineer wishes to control. The mutation is a short sequence that transcribes into the 5'-untranslated region of the mRNA a nucleotide sequence complementary to the ribosome binding site. Hybridization then prevents the ribosome from recognizing the messenger.

Sumimoto et al., in *Future Oncol.*, 3(6):655-64, (2007) and Sumimoto et al., in *Int. J. Cancer*, 118(2):472-6, (2006) have introduced siRNA, as such, into cells by means of lentiviral vectors, and Wiznerozicz et al., in *J. Virol.*, 77(16): 8957-8961, (2003) similarly introduced a construct that can be induced by drugs to express siRNA, but neither of these references suggests coupling siRNA expression to endogenous signals.

Not all living cells are under the control of a normally functioning control system. Cancer cells, for example, have a dysfunctional control system. Normal cells exchange and process numerous molecular signals in a generally coordinated fashion that is reflected in the ongoing integrity of the cell. Even when one or more of these signals is faulty, a normal cell readily detects the fault and initiates self-repair processes or, when necessary, apoptosis. Current cancer therapies such as surgery, chemotherapy and radiation treatment are highly aggressive methods of killing cells, notorious for causing collateral damage and equally notorious for missing their targets. What is needed are treatments directed at restoring enough self-control to cancerous cells, wherever they may be located in a patient's body, to allow them at least to eliminate themselves.

SUMMARY

In some embodiments, the invention provides a composition, the composition comprising a vector for transfecting a cell, the vector comprising:
  a) a first nucleic acid encoding an antisense agent, said antisense agent comprising an RNA interference target for a transcript of a gene endogenous to the cell, and
  b) a second nucleic acid encoding a cell-killing agent, said second nucleic acid comprising a sequence of nucleotides transcribable into a non-coding region of a transcript of said second nucleic acid, said non-coding region comprising an RNA interference target for said antisense agent.

In one embodiment, the cell is a cancer cell.

In one embodiment, the antisense agent is selected from the group consisting of a siRNA, a shRNA, a microRNA, a ribozyme, and an aptamer.

In some embodiments, the composition comprises a plurality of antisense agents.

In a preferred embodiment, the endogenous gene is selected from the group consisting of Gata3, NPY1R and TFF1.

In some embodiments, the cell-killing agent is a protein.

In some embodiments, the composition comprises a plurality of cell-killing agents.

In one embodiment, the cell-killing agent is an apoptotic agent.

In one embodiment, the endogenous gene is overexpressed in the cell.

In one embodiment, the endogenous gene is underexpressed in the cell.

In one embodiment, the vector of the composition comprises an inducible promoter operatively linked to the first nucleic acid.

In one embodiment, the vector of the composition comprises an inducible promoter operatively linked to the second nucleic acid.

In one embodiment, the vector is a viral vector.

In one embodiment, the vector is a lentiviral vector.

In one embodiment, the lentiviral vector comprises a non-integrating integrase.

In other embodiments, the invention provides a method of killing a cell by the step of exposing said cell to a composition according to claim 1.

In one embodiment, the invention provides a method of treating a patient with a cell-killing composition comprising:
  a) providing
    i) a patient having a symptom or symptoms suggesting a need of such treatment, and
    ii) a composition according to claim 1, and
  b) administering the composition to the patient under conditions such that the composition ameliorates the symptom or symptoms.

In another embodiment, the invention provides a kit comprising the composition of claim 1 and a set of instructions for use.

In preferred embodiments, overexpression or underexpression of the endogenous gene is a biomarker of a disease. In more preferred embodiments, the biomarker is an overexpression or underexpression of a plurality of endogenous genes.

In some embodiments, the antisense agent is a nucleic acid comprising:
  a) a first nucleotide sequence complementary, preferably with mismatches, to an endogenous gene that is a biomarker for a disease, and
  b) a second nucleotide sequence complementary, preferably at high stringency, to a nucleotide sequence in a non-coding region of a transcript of a gene that encodes a cell-killing protein.

In a preferred embodiment, a plurality of antisense agents, each agent comprising: (a) a first nucleotide sequence that is an RNA interference target for a transcript of one and only one of a plurality of endogenous genes, which endogenous genes, in combination, comprise a biomarker for a disease, and (b) a second nucleotide sequence that binds to an RNA interference target in a non-coding region of a transcript of a gene that encodes a cell-killing protein, in operation as a plurality, inhibits expression of the cell-killing protein in the absence of the biomarker and, in the presence of the biomarker, is severally destroyed.

In another embodiment, the invention provides a method, comprising:
  a) providing
    i) a subject having cancer cells and non-cancer cells, said cancer cells transcribing a gene not transcribed in said non-cancer cells, said transcribing creating a cancer gene RNA transcript;
    ii) a vector comprising first and second nucleic acid sequences, said first nucleic acid sequence comprising first and second regions, said first region having an RNA transcript complementary to a region of said cancer gene RNA transcript, said second region having an RNA transcript complementary to an RNA transcript of a first region of said second nucleic acid sequence, said second nucleic acid sequence further comprising a second region having an RNA transcript encoding a cell-killing protein, and
  b) transfecting said cancer cells and non-cancer cells of said subject under conditions such that said cancer gene RNA transcript binds to said first region of said first nucleic acid sequence under conditions such that
    (i) the RNA transcript of said second region is digested,
    (ii) the RNA transcript encoding said cell-killing protein increases in concentration, and (iii) the protein encoded in said second nucleic acid sequence is expressed in an amount sufficient to kill at least a portion of said cancer cells, wherein said transfected non-cancer cells are not killed.

BRIEF DESCRIPTION OF THE DRAWINGS

FIG. 5: Gata3 RNAi sequence design [SEQ ID NOs:1-10]. The siRNA sequences, designed using a Perl program written by the inventors (based on [37]), are optimized to degrade target site mRNA and be titrated by the biomarker without affecting protein translation. We match the target site exactly and introduce mismatches against biomarker sequences in positions 1, 8, 9 or 1, 2, 8 [38]. The library of potential sequences were checked for secondary structure and binding free energy using the Vienna RNA package. MiR-661 siRNA is known to bind and inactivate endogenous Gata3 mRNA and is included as a control [39] [SEQ ID NOs:11-15].

DEFINITIONS

Figure 1:
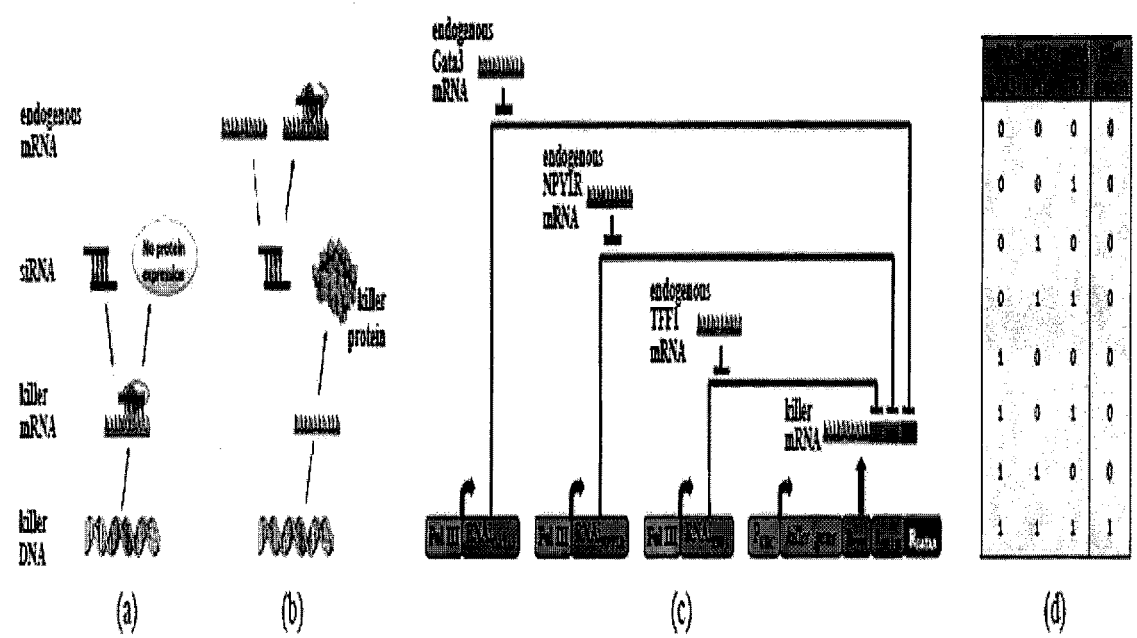
FIG. 1 RNAi logic circuit-based approach. (a-b) Killer protein (e.g. Bax and Bak [3, 29-32]) expression depends on levels of endogenous marker mRNA as mediated by siRNA interactions. (c) For the 3-input AND gate, the endogenous levels of Gata3, NPY1R and TFF1 all need to be high in order to titrate away the three engineered siRNAs and allow expression of the killer protein. (d) Truth table showing how the AND gate operation, i.e. killer protein expression, depends on the presence of all three biomarkers.

To facilitate the understanding of this invention a number of terms (set off in quotation marks in this Definitions section) are defined below. Terms defined herein (unless otherwise specified) have meanings as commonly understood by a person of ordinary skill in the areas relevant to the present invention. As used in this specification and its appended claims, terms such as "a", "an" and "the" are not intended to refer to only a singular entity or element, but include the general class of which a specific example may be used for illustration, unless the context dictates otherwise. A "plurality" of elements herein refers to a condition wherein more than a single element is necessary. "Plurality" may refer to a plurality of identical elements or to a plurality of elementary classes as the context so admits. The terminology herein is used to describe specific embodiments of the invention, but their usage does not delimit the invention, except as outlined in the claims.

The phrase "chosen from A, B, and C" as used herein, means selecting one or more of A, B, C. The phrase is equivalent to "selected from the group consisting of A, B and C." The phrase "A, B and C in combination" implies the presence of all three elements.

As used herein, absent an express indication to the contrary, the term "or" when used in the expression "A or B," where A and B refer to a composition, disease, product, etc., means one or the other, or both. As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the context clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weights, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (mRNA, etc.) or phenomenon (such as biological activity, biochemical activity, etc.) means that only the particularly named molecule or phenomenon is excluded.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

The terms "increase," "elevate," "raise," and grammatical equivalents when used in reference to the level of a substance and/or phenomenon in a first sample relative to a second sample, mean that the quantity of the substance and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, clarity of vision, etc. In another embodiment, the quantity of the substance and/or phenomenon in the first sample is at least 10% greater than the quantity of the same substance and/or phenomenon in a second sample. In another embodiment, the quantity of the substance and/or phenomenon in the first sample is at least 25% greater than the quantity of the same substance and/or phenomenon in a second sample. In yet another embodiment, the quantity of the substance and/or phenomenon in the first sample is at least 50% greater than the quantity of the same substance and/or phenomenon in a second sample. In a further embodiment, the quantity of the substance and/or phenomenon in the first sample is at least 75% greater than the quantity of the same substance and/or phenomenon in a second sample. In yet another embodiment, the quantity of the substance and/or phenomenon in the first sample is at least 90% greater than the quantity of the same substance and/or phenomenon in a second sample. Alternatively, a difference may be expressed as an "n-fold" difference.

The terms "reduce," "inhibit," "diminish," "suppress," "decrease," and grammatical equivalents when used in reference to the level of a substance and/or phenomenon in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, clarity of vision, etc. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample. Alternatively, a difference may be expressed as an "n-fold" difference.

"Subject" and "patient" are used herein interchangeably, and a subject may be any mammal but is preferably a human. A "reference subject" herein refers to an individual who does not have a disease. A "healthy subject" is an equivalent term herein. The "reference subject" thereby provides a basis against which a symptom or a cell, tissue, etc. of the patient can be compared.

A number of terms herein relate to cancer. "Cancer" is intended herein to encompass all forms of abnormal or improperly regulated reproduction of cells in a subject. The growth of cancer cells ("growth" herein referring generally to cell division but also to the growth in size of masses of cells) is characteristically uncontrolled or inadequately controlled. For example, well-known processes that contribute to the control of healthy cells by "repairing" damaged DNA (and, potentially, the genetic code of the cell) may be faulty in cancer cells. Also, the biological system that provides for an "orderly" death of normal cells ("apoptosis"), mediated by one or more apoptotic proteins, may be compromised. The terms "killer," "kill signal," "kill message," and "cell-killing" in connection with proteins or other agents include but are not limited to apoptotic proteins. Local accumulations of control-deficient cells result in a tumor. More broadly, and still denoting "tumors" herein are accumulations ranging from a cluster of lymphocytes at a site of infection to vascularized overgrowths, both benign and malignant. A "malignant" tumor (as opposed to a "benign" tumor) herein comprises cells that tend to migrate to nearby tissues, including cells that may travel through the circulatory system to invade or colonize tissues or organs at considerable remove from their site of origin in the "primary tumor," so-called herein. Metastatic cells are adapted to penetrate blood vessel wells to enter ("intravasate") and exit ("extravasate") blood vessels. Tumors capable of releasing such cells are also referred to herein as "metastatic." The term is used herein also to denote any cell in such a tumor that is capable of such travel, or that is en route, or that has established a foothold in a target tissue. For example, a metastatic breast cancer cell that has taken root in the lung is referred to herein as a "lung metastasis." Metastatic cells may be identified herein by their respective sites of origin and destination, such as "breast-to-bone metastatic." In the target tissue, a colony of metastatic cells can grow into a "secondary tumor," so called herein.

Primary tumors are thought to derive from a benign or normal cell through a process referred to herein as "cancer progression." According to this view, the transformation of a normal cell to a cancer cell requires changes (usually many of them) in the cell's biochemistry. Such changes are reflected in changes in so-called "metabolic indicators," often monitored experimentally and clinically by following changes in the expression of genes such as caseins a and g (csna, csng), fatty acid bp4 (fabp4), carbonic anhydrases 3 and 6 (Car3, Car6), whey acidic protein (wap), lipoprotein lipase (lpl), zinc finger protein 503 (zfp503), adipsin (and), thyroid SPOT14 homologue (thrsp), lactalbumin a (lalba), sterol carrier protein 2 (scp2), acyl-CoA synthetase L4 (acs14), CDC-like kinase 1 (clk1), catenin D1 (ctnnd1) and tumor differentially expressed protein 1 tumor differential expression 1 (tde1). ( )—a transmembrane protein.

Even if a tumor is "clonogenic" (as used herein, an accumulation of the direct descendants of a parent cell), the biochemistry of the accumulating cells changes in successive generations, both because the expression of the genes (controlled by so-called "epigenetic" systems) of these cells becomes unstable and because the genomes themselves change. In normal somatic cells, the genome (that is, all the genes of an individual) is stored in the chromosomes of each cell (setting aside the mitochondrial genome). The number of copies of any particular gene is largely invariant from cell to cell. By contrast, "genomic instability" is characteristic of cancer progression. A genome in a cancer cell can gain ("genomic gain") or lose ("genomic loss") genes, typically because an extra copy of an entire chromosome appears ("trisomy") or a region of a chromosome replicates itself ("genomic gain" or, in some cases, "genomic amplification") or drops out when the cell divides. Thus, the "copy number" of a gene or a set of genes, largely invariant among normal cells, is likely to change in cancer cells (referred to herein as a "genomic event"), which affects the total expression of the gene or gene set and the biological behavior ("phenotype") of descendent cells. Thus, in cancer cells, "gene activity" herein is determined not only by the multiple "layers" of epigenetic control systems and signals that call forth expression of the gene but by the number of times that gene appears in the genome. The term "epigenetic" herein refers to any process in an individual that, in operation, affects the expression of a gene or a set of genes in that individual, and stands in contrast to the "genetic" processes that govern the inheritance of genes in successive generations of cells or individuals.

A number of terms herein relate to methods that enable the practitioner to examine many distinct genes at once. By these methods, sets of genes ("gene sets") have been identified wherein each set has biologically relevant and distinctive properties as a set. Devices (which may be referred to herein as "platforms") in which each gene in a significant part of an entire genome is isolated and arranged in an array of spots, each spot having its own "address," enable one to detect, quantitatively, many thousands of the genes in a cell. More precisely, these "microarrays" typically detect expressed genes (an "expressed" gene is one that is actively transmitting its unique biochemical signal to the cell in which the gene resides). Microarray data, inasmuch as they display the expression of many genes at once, permit the practitioner to view "gene expression profiles" in a cell and to compare those profiles cell-to-cell to reveal "differential gene expression profiles" on which so-called "comparative analyses of expression profiles" are performed. Such microarray-based "expression data" are capable of identifying genes that are "overexpressed" (or underexpressed) in, for example, a disease condition. An overexpressed gene may be referred to herein as having a high "expression score."

A gene is a potentially heritable chemical code resident in, for example, a cell, virus, or bacteriophage that an organism utilizes as a template for ordering (decoding, decrypting, transcribing, translating) the structures of biomolecules that an organism synthesizes to impart regulated function to the organism. Chemically, a gene is a heteropolymer comprised of subunits arranged in a specific sequence. Each such subunit is essentially a sugar molecule covalently linked to a nitrogen-containing organic molecule (either a purine or a pyrimidine) that, by itself, acts as a base in aqueous solution. These "nucleotides" ("nucleobases" or simply "bases") polymerize in cells into deoxynucleic acids ("DNA") or ribonucleic acids ("RNA"). The nucleotides are arranged in a plurality of particular sequences, each sequence comprising a "genetic code" necessary for the production of a polypeptide or polypeptide precursor or RNA (e.g., tRNA, siRNA, rRNA, etc.) and, especially, messenger RNA ("mRNA"). The cell can read or "translate" each genetic message into a polypeptide (or protein). Conventionally (but not universally), the heritable genetic code is embedded in DNA, "transcribed" into a non-heritable genetic code embedded in RNA (referred to herein as a "transcript"), and finally "translated" from the "language" of nucleic acids (i.e., sequences of nucleotides) to the language of polypeptides (i.e., sequences of amino acids). Polypeptides are polymers comprising amino acid subunits. Polypeptides, acting together in an organism, give final, operative expression to the genetic code of the organism. A polypeptide can be encoded by a full-length nucleic acid coding sequence or by any portion of the coding sequence so long as the desired activities or functional properties (e.g., enzymatic activity, ligand binding, signal transduction, etc.) are retained. The term "gene" encompasses the coding region together with the sequences located adjacent to the coding region on both the 5' and 3' ends, such that the gene corresponds to the length of the full-length mRNA (also referred to as "pre-mRNA," "nuclear RNA," or "primary transcript RNA") transcribed from it. Sequences located 5' of the coding region and present on the mRNA are referred to as 5' untranslated sequences. Sequences located 3' or downstream of the coding region (the cell "reads" nucleic acid molecules from the so-called 5' end of the molecule to the 3' end) and that are present on the mRNA are referred to as 3' untranslated sequences. The term "gene" encompasses both cDNA (the coding region(s) only) and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

Collectively, the genes of an organism constitute its genome. The term "genomic DNA" may refer herein to an organism's DNA in its collective entirety or, more narrowly, to the entirety of the nucleotides comprising a single gene in an organism. The term "non-coding region," as used herein extends beyond introns to encompass any nucleic acid sequence that does not directly encode all or part of a gene. In particular contexts herein, the term "non-coding region" refers specifically to the aforementioned 5'- and 3'-untranslated regions of mRNA DNA forms long strands. Characteristically, these strands occur in pairs. The first member of a pair is not identical in nucleotide sequence to the second strand, but complementary. The tendency of a first strand to bind in this way to a complementary second strand (the two strands are said to "anneal" or "hybridize"), together with the tendency of individual nucleotides to line up against a single strand in a complementarily ordered manner accounts for the replication of DNA. One of the strands encodes heritable genetic information and is called a "sense" (or "positive sense") strand. From the other, called the "anti-sense" (or "negative sense") strand, is transcribed "sense RNA." The term "anti-sense" may refer to a structure or, when the context so admits, a function. For example, any agent that affects a function of a nucleic acid by binding to it due to nucleotide sequence complementarity between agent and nucleic acid is an "antisense" function of the agent.

Experimentally, nucleotide sequences selected for their complementarity can be made to anneal to a strand of DNA containing one or more genes. A single such sequence can be employed to identify the presence of a particular gene by attaching itself to the gene. This so-called "probe" sequence is adapted to carry with it a "marker" that the investigator can readily detect as evidence that the probe struck (bound to) a target. As used herein, the term "marker" relates to any surrogate the artisan may use to "observe" a structure, event or condition that is difficult or impossible to detect directly.

"Encoding" in DNA (and messenger RNA) is accomplished by 3-membered nucleotide sequences called "codons." Each codon encrypts an amino acid, and the sequence of codons encrypts the sequence of amino acids that identifies a particular protein. The code for a given gene is embedded in a (usually) much longer nucleotide sequence. and is distinguishable to The cell's decoding system distinguishes the gene from the longer sequence by a "start codon" and a "stop" codon. The decoding system reads the sequence framed by these two codons (the so-called "open reading frame"). The readable code is transcribed into messenger RNA which itself comprises sites that ensure coherent translation of the code from nucleic acid to protein. In particular, the open reading frame is delimited by a so-called "translation initiation" site and a "translation termination" site.

The term "plasmid" as used herein, refers to a small, independently replicating, piece of DNA. Similarly, the term "naked plasmid" refers to plasmid DNA devoid of extraneous material typically used to effect transfection. As used herein, a "naked plasmid" refers to a plasmid substantially free of calcium-phosphate, DEAE-dextran, liposomes, and/or polyamines. As used herein, the term "purified" refers to molecules (polynucleotides or polypeptides) that are removed from their natural environment, isolated or separated. "Purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA.

The term "fusion protein" as used herein refers to a protein formed by expression of a hybrid gene made by combining two gene sequences. Typically this is accomplished by cloning a cDNA into an expression vector in frame (i.e., in an arrangement that the cell can transcribe as a single mRNA molecule) with an existing gene. The fusion partner may act as a reporter (e.g., βgal, enhanced green fluorescent protein or "EGFP") or may provide a tool for isolation purposes.

Where an amino acid sequence is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Rather the terms "amino acid sequence" and "protein" encompass partial sequences, and modified sequences.

The term "wild type" refers to a gene or gene product that has the characteristics of that gene or gene product when isolated from a naturally occurring source. A wild type gene is the variant most frequently observed in a population and is thus arbitrarily designed the "normal" or "wild-type" form of the gene In contrast, the terms "modified," "mutant," and "variant" (when the context so admits) refer to a gene or gene product that displays modifications in sequence and or functional properties (i.e., altered characteristics) when compared to the wild-type gene or gene product. In some embodiments, the modification comprises at least one nucleotide insertion, deletion, or substitution.

The term "homology" refers to a degree of complementarity. There may be partial homology or complete homology (i.e., identity). A partially complementary sequence is one that at least partially inhibits a completely complementary sequence from hybridizing. Such a sequence in a nucleic acid is referred to using the functional term "substantially homologous." The term "inhibition of binding," when used in reference to nucleic acid binding, refers to reduction in binding caused by competition of homologous sequences for binding. The extent of inhibition of hybridization of the completely complementary sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" when used in reference to a first and a second polypeptide means that the first polypeptide with an activity binds to the same substrate as does the second polypeptide with an activity. In one embodiment, the second polypeptide is a variant of the first polypeptide (e.g., encoded by a different allele) or a related (e.g., encoded by a homolog) or dissimilar (e.g., encoded by a second gene having no apparent relationship to the first gene) polypeptide. The efficiency (e.g., kinetics or thermodynamics) of binding by the first polypeptide may be the same as or greater than or less than the efficiency of substrate binding by the second polypeptide. For example, the equilibrium binding constant ($K_D$) for binding to the substrate may be different for the two polypeptides.

As used herein, the term "hybridization" refers to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with 85-100% identity, preferably 70-100% identity). With medium stringency conditions, nucleic acid base pairing will occur between nucleic acids with an intermediate frequency of complementary base sequences (e.g., hybridization under "medium stringency" conditions may occur between homologs with 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 100 to about 1000 nucleotides in length is employed.

"Medium stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C. when a probe of about 100 to about 1000 nucleotides in length is employed.

"Low stringency conditions" comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

The following terms are used to describe the sequence relationships between two or more polynucleotides: "reference sequence," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.*, 2: 482, 1981) by the homology alignment algorithm of Needleman and Wunsch (Needleman and Wunsch, *J. Mol. Biol.*, 48:443, 1970), by the search for similarity method of Pearson and Lipman (Pearson and Lipman, *Proc. Natl. Acad. Sci., U.S.A.*, 85:2444, 1988), by computerized implementations of these algorithms (GAP, BESTFIT, FASTA, and TFASTA in the Wisconsin Genetics Software Package Release 7.0, Genetics Computer Group, Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is glutamic acid and aspartic acid; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method The term "target," when used in reference to the polymerase chain reaction, refers to the region of a nucleic acid bounded by the primers used in the reaction. A "segment" is defined as a region of nucleic acid within the target sequence.

As used herein, the term "polymerase chain reaction" ("PCR") refers to the method of Mullis (U.S. Pat. Nos. 4,683,195, 4,683,202, and 4,965,188, hereby incorporated by reference), that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." A specific nucleotide sequence so amplified is referred to herein as the "amplicon" of that sequence. "Quantitative PCR" or "qPCR" (also "Q-PCR") herein refers to a version of the method that allows the artisan not only to detect the presence of a specific nucleic acid sequence but also to quantify how many copies of the sequence are present in a sample, at least relative to a control. As used herein, "qRTPCR" may refer to "quantitative real-time PCR," used interchangeably with "qPCR" as a technique for quantifying the amount of a specific DNA sequence in a sample. However, if the context so admits, the same abbreviation may refer to "quantitative reverse transcriptase PCR," a method for determining the amount of messenger RNA present in a sample. Since the presence of a particular messenger RNA in a cell indicates that a specific gene is currently active (being expressed) in the cell, this quantitative technique finds use, for example, in gauging the level of expression of a gene.

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding gene includes, by way of example, such nucleic acid in cells ordinarily expressing gene where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

The terms "fragment" and "portion" when used in reference to a nucleotide sequence (as in "a portion of a given nucleotide sequence") refers to partial segments of that sequence. The fragments may range in size from four nucleotides to the entire nucleotide sequence minus one nucleotide (10 nucleotides, 20, 30, 40, 50, 100, 200, etc.).

Similarly, the terms "fragment" and "portion" when used in reference to a polypeptide sequence refers to partial segments of that sequence. In some embodiments, the portion has an amino-terminal and/or carboxy-terminal deletion as compared to the native protein, but where the remaining amino acid sequence is identical to the corresponding positions in the amino acid sequence deduced from a full-length cDNA sequence. Fragments are preferably at least 4 amino acids long, more preferably at least 50 amino acids long, and most preferably at least 50 amino acids long or longer (the entire amino acid sequence minus on amino acid). In particularly preferred embodiments, the portion comprises the amino acid residues required for intermolecular binding of the compositions of the present invention with its various ligands and/or substrates.

As used herein the term "portion" when in reference to a protein (as in "a portion of a given protein") refers to fragments of that protein. The fragments may range in size from four consecutive amino acid residues to the entire amino acid sequence minus one amino acid As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA The term "native protein" as used herein to indicate that a protein does not contain amino acid residues encoded by vector sequences, that is the native protein contains only those amino acids found in the protein as it occurs in nature. A native protein may be produced by recombinant means or may be isolated from a naturally occurring source.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, NY, pp 9.31-9.58, 1989).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp 7.39-7.52, 1989).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies As used herein, the term "transgenic" refers to a cell or organism whose genome has been heritably altered by genetically engineering into the genome a gene ("transgene") not normally part of it or removing from it a gene ordinarily present (a "knockout" gene). The "transgene" or "foreign gene" may be placed into an organism by introducing it into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer nucleic acid segment(s) (DNA or RNA) to or into a cell. The term "vehicle" is sometimes used interchangeably with "vector." As the context will make clear, the term "vector" may be used herein to refer to the means by which the nucleic acid vector is brought to a cell for transfer or introduced into the cell. The term "transfection" as used herein refers to the introduction of foreign DNA (or RNA) into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

In preferred embodiments herein, a lentiviral vector is used. Lentiviruses are "RNA viruses." That is, their genomes are encoded in RNA instead of DNA. However, reverse transcriptase, an enzyme intrinsic to the virus (that is, encoded in the viral genome, not "co-opted" from the host genome), catalyzes the conversion of the RNA into DNA upon the virus's entry into a cell. Another intrinsic viral enzyme, integrase, then shuttles the DNA into the nucleus of the cell (by means of a "nuclear import signal" that is part of the lentivirus (or, more specifically, part of the viral "pre-integration complex") and catalyzes its integration into the cellular genome. Several well-known mutations of integrase, however, retain the shuttling function but lack the integrating function. They are "non-integrating" integrases.

The term "expression vector" as used herein refers to a recombinant DNA (or RNA) molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. A "promoter" is a nucleotide sequence in a nucleic acid associated with a gene in such a way that RNA synthesis can proceed under catalysis by RNA polymerase.

The designer of an expression vector can usually choose among a number of promoters to accompany any particular transgene. In some embodiments of the present invention, one may select an inducible promoter, i.e., a promoter that will not work unless an externally applied factor is present. A large number of these are well-known in the art, many of which are commercially available in forms especially adapted for splicing into expression vectors.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal. The term "host cell" encompasses both normal and abnormal cells including, without limitation, cancer cells.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell in the sense that the foreign DNA will be passed on to daughter cells. The term encompasses transfections of foreign DNA into the cytoplasm only. In general, however, the foreign DNA reaches the nucleus of the transfected cell and persists there for several days. During this time the foreign DNA is subject to the regulatory controls that govern the expression of endogenous ("arising from within" a cell, organism or tissue as the context so admits) genes in the chromosomes. The term "transient transfectant" refers to cells that have taken up foreign DNA but have failed to integrate this DNA. The term "transient transfection" encompasses transfection of foreign DNA into the cytoplasm only.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of is modified to optimize conditions for particular types of cells. The art is well aware of these numerous modifications.

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.

The terms "antigen," "immunogen," "antigenic," "immunogenic," "antigenically active," and "immunologically active" refer to any substance that is capable of inducing a specific humoral and/or cell-mediated immune response. An immunogen generally contains at least one epitope. Immunogens are exemplified by, but not restricted to molecules which contain a peptide, polysaccharide, nucleic acid sequence, and/or lipid. Complexes of peptides with lipids, polysaccharides, or with nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves.

A peptide sequence and nucleotide sequence may be "endogenous" or "heterologous" (i.e., "foreign" or "exogenous"). The term "endogenous" refers to a sequence which is naturally found in the cell or virus into which it is introduced so long as it does not contain some modification relative to the naturally-occurring sequence. The term "heterologous" refers to a sequence which is not endogenous to the cell or virus into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell or virus into which it is introduced and which contains some modification relative to the naturally-occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc. In preferred embodiments, the terms "heterologous antigen" and "heterologous sequence" refer to a non-hepadna virus antigen or amino acid sequence including but not limited to microbial antigens, mammalian antigens and allergen antigens.

The terms "peptide," "peptide sequence," "amino acid sequence," "polypeptide," and "polypeptide sequence" are used interchangeably herein to refer to at least two amino acids or amino acid analogs which are covalently linked by a peptide bond or an analog of a peptide bond. The term peptide includes oligomers and polymers of amino acids or amino acid analogs. The term peptide also includes molecules which are commonly referred to as peptides, which generally contain from about two (2) to about twenty (20) amino acids. The term peptide also includes molecules which are commonly referred to as polypeptides, which generally contain from about twenty (20) to about fifty amino acids (50). The term peptide also includes molecules which are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide which is produced by artificial means in vitro As used herein, the term "mammalian sequence" refers to synthetic, recombiant or purified sequences (preferably sequence fragments comprising at least one B cell epitope) of a mammal. Exemplary mammalian sequences include cytokine sequence, MHC class I heavy chain sequences, MHC class II alpha and beta chain sequences, and amyloid β-peptide sequences.

The terms "mammals" and "mammalian" refer animals of the class mammalia which nourish their young by fluid secreted from mammary glands of the mother, including human beings. The class "mammalian" includes placental animals, marsupial animals, and monotrematal animals. An exemplary "mammal" may be a rodent, primate (including simian and human) ovine, bovine, ruminant, lagomorph, porcine, caprine, equine, canine, feline, ave, etc. Preferred non-human animals are selected from the order Rodentia.

Preferred embodiments of the present invention are primarily directed to vertebrate (backbone or notochord) members of the animal kingdom.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to a subject that which receives a mock treatment.

The terms "diluent" and "diluting agent" as used herein refer to agents used to diminish the strength of an admixture. Exemplary diluents include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

The terms "carrier" and "vehicle" as used herein refer to usually inactive accessory substances into which a pharmaceutical substance is suspended. Exemplary carriers include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

The term "derived" when in reference to a peptide derived from a source (such as a microbe, cell, etc.) as used herein is intended to refer to a peptide which has been obtained (e.g., isolated, purified, etc.) from the source. Alternatively, or in addition, the peptide may be genetically engineered and/or chemically synthesized.

The terms "operably linked," "in operable combination," and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking a nucleic acid sequence encoding a protein of interest means linking the nucleic acid sequence to regulatory and other sequences in a manner such that the protein of interest is expressed. The term also refers to the linkage of amino acid sequences in such a manner so that a functional protein is produced.

The terms "C-terminal portion," "COOH-terminal portion," "carboxy terminal portion," "C-terminal domain," "COOH-terminal domain," and "carboxy terminal domain," when used in reference to an amino acid sequence of interest refer to the amino acid sequence (and portions thereof that is located from approximately the middle of the amino acid sequence of interest to the C-terminal-most amino acid residue of the sequence of interest. The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule.

"Specific binding" of a first molecule with a second molecule also means that the interaction between the first molecule and the second molecule is dependent upon the presence of a particular structure on or within the first molecule; in other words the second molecule is recognizing and binding to a specific structure on or within the first molecule rather than to nucleic acids or to molecules in general. For example, if a second molecule is specific for structure "A" that is on or within a first molecule, the presence of a third nucleic acid sequence containing structure A will reduce the amount of the second molecule which is bound to the first molecule.

For example, the term "has the biological activity of a specifically named protein," when made in reference to the biological activity of a variant of the specifically named protein refers, for example, to a quantity of binding of an antibody that is specific for the specifically named protein to the variant which is preferably greater than 50% (preferably from 50% to 500%, more preferably from 50% to 200%, most preferably from 50% to 100%), as compared to the quantity of binding of the same antibody to the specifically named protein.

Reference herein to any specifically named nucleotide sequence includes within its scope fragments, homologs, and sequences that hybridize under stringent condition to the specifically named nucleotide sequence. The term "homolog" of a specifically named nucleotide sequence refers to an oligonucleotide sequence which exhibits greater than or equal to 50% identity to the sequence of interest. Alternatively, or in addition, a homolog of any specifically named nucleotide sequence is defined as an oligonucleotide sequence which has at least 95% identity with the sequence of the nucleotide sequence in issue. In another embodiment, the sequence of the homolog has at least 90% identity, and preferably at least 85% identity with the sequence of the nucleotide sequence in issue.

The term "agent" is used herein in its broadest sense to refer to a composition of matter, a process or procedure, a device or apparatus employed to exert a particular effect. By way of non-limiting example, a surgical instrument may be employed by a practitioner as an "excising" agent to remove tissue from a subject; a chemical may be used as a pharmaceutical agent to remove, damage or neutralize the function of a tissue, etc. Such pharmaceutical agents are said to be "anticellular." Cells may be removed by an agent that promotes apoptosis. A variety of toxic agents, including other cells (e.g., cytotoxic T-cell lymphocytes) and their secretions, and a plethora of chemical species, can damage cells.

The term "by-stander", as used herein, refers to a process or event initiated or affected by another, causative event or process The term "knockdown", as used herein, refers to a method of selectively preventing the expression of a gene in an individual.

The term "oncogene", as used herein, refers to any gene that regulates a process affecting the suppression of abnormal proliferative events.

The term "single nucleotide polymorphism" or "SNP", as used herein, refers to a DNA sequence variation occurring when a single nucleotide in the genome (or other shared sequence) differs between members of a species or between paired chromosomes in an individual. Single nucleotide polymorphisms may fall within coding sequences of genes, non-coding regions of genes, or in the intergenic regions between genes. Single nucleotide polymorphisms within a coding sequence will not necessarily change the amino acid sequence of the protein that is produced, due to degeneracy of the genetic code. A Single nucleotide polymorphism in which both forms lead to the same polypeptide sequence is termed synonymous (sometimes called a silent mutation)— if a different polypeptide sequence is produced they are non-synonymous. Single nucleotide polymorphisms that are not in protein-coding regions may still have consequences for gene splicing, transcription factor binding, or the sequence of non-coding RNA.

The term "algorithm", as used herein, refers to a step-by-step problem-solving procedure, especially an established, recursive computational procedure for solving a problem in a finite number of steps.

The term "tissue array" or "tissue microarray", as used herein, refers to high throughput platforms for the rapid analysis of protein, RNA, or DNA molecules. These arrays can be used to validate the clinical relevance of potential agents for use in diagnostics, therapeutics and to study new disease markers and genes.

As used herein, the term "shRNA" or "short hairpin RNA" refers to a sequence of ribonucleotides comprising a single-stranded RNA polymer that makes a tight hairpin turn on itself to provide a "double-stranded" or duplexed region. shRNA can be used to silence gene expression via RNA interference. The shRNA hairpin is cleaved into short interfering RNAs (siRNA) by the cellular machinery and then bound to the RNA-induced silencing complex (RISC). It is believed that the complex inhibits RNA as a consequence of the complexed siRNA hybridizing to and cleaving RNAs that match the siRNA that is bound thereto.

As used herein, the term short interfering RNA ("siRNA") refers to a relatively short, double-stranded RNA about 18-25 nucleotides long; often siRNAs contain from about two to four unpaired nucleotides at the 3' end of each strand. In some embodiments, at least one strand of the duplex or double-stranded region of a siRNA is substantially homologous to or substantially complementary to a particular species of RNA molecule. The strand complementary to that RNA molecule is the "antisense strand." siRNAs may also contain additional sequences. Non-limiting examples include linking sequences, or loops, as well as stem and other folded structures. SiRNAs appear to function as key intermediaries in triggering RNA interference in invertebrates and in vertebrates, and in triggering sequence-specific RNA degradation during posttranscriptional gene silencing in plants.

As used herein, the term "RNA interference" or "RNAi" is used broadly to refer to a silencing or diminution of gene expression because part of the nucleotide sequence of an RNA transcript functions so as to lead to failure of the transcript to translate into a protein, that is through an "antisense" process (see below). Under this definition, the post-transcriptional gene silencing in animals and plants that is initiated by siRNA is but one form of RNA interference. Any sequence in an RNA molecule that marks it for a translation-disabling attack is an "RNA interference target" herein.

SiRNA leads to RNA interference through the agency of the so-called RNA-induced silencing complex ("RISC"), a sequence-specific, multicomponent nuclease that destroys messenger RNA having substantial homology to the silencing molecule. The latter, in order to be a silencing molecule, must have a sequence that is homologous to the sequence of the gene that encoded the mRNA. The siRNA can itself be a transcription product of a gene, and that gene may be endogenous or heterologous, present integrated into a chromosome or present in a transfection vector that is not integrated into the genome.

In nature, siRNA is rare. It appears to arise from the complementary duplication of a relatively long single-stranded RNA (perhaps the RNA of an invading virus, for example). The RISC complex digests the product into short RNAs (approximately 22). If among the digestion products there is a short RNA that binds to a messenger RNA, the RISC complex recognizes that mRNA as a substrate and digests it. The gene for which the mRNA was the messenger is thus silenced (Carthew in *Curr. Opin. Cell Biol.* 13(2): 244-248 (2001)).

"Antisense," as used herein, encompasses the concept of preventing information encoded in a polymeric biomolecule from being biologically interpreted or decoded. Such information is embodied in a particular sequence of the subunits (or "mers") that comprise the biomolecule. The sequence encoding the information is referred to as a "sense sequence" because it directly encodes the genetic information that a cell ultimately expresses as a protein. Contacting a sense sequence with an "antisense sequence" can interfere with the biological decoding of the information in the sense sequence, typically because the sense sequence and the antisense sequence bind to one another. "Binding" refers to chemical interactions between the two sequences that leave the two in a more stable state, energetically, than they are when not "bound." The complementarity of such sequences accounts in large part for the binding energy. If each unit in the sense sequence is optimally matched energetically to each unit in the antisense sequence, complementarity is maximized. "Mismatches" tend to reduce the binding affinity. The double-stranded DNA that comprises chromosomes is but one example of a sense-antisense pair in which the antisense strand "interferes" with the transcription of the genetic information in the sense strand into messenger ribonucleic acid ("mRNA"). The genetic information, at this stage, may be referred to herein as the "genetic message."

A wide variety of molecules can interfere, by one or another of several mechanisms, with the decoding of "sense." Very broadly, any agent that disrupts the normal flow of the genetic code from genotype to phenotype is an "antisense agent." More narrowly, as noted above, any agent that affects a function of a nucleic acid by binding to it on account of nucleotide sequence complementarity between agent and nucleic acid is an "antisense" agent. In preferred embodiments of the invention, mRNA, in which is encoded the amino acid structure of proteins, is interfered with. The interfering molecule may be, for example, a short RNA molecule having a nucleotide sequence that is generally complementary to the messenger RNA. So-called short siRNA, shRNA, and micro RNA ("miRNA") are non-limiting examples. Ribozymes (RNA molecules with catalytic activity), aptamers (short sequences of DNA, RNA or amino acids) and single stranded DNA ("ssDNA") may also function in this manner. Just as the nucleotide sequence of an mRNA is encoded (typically) in deoxyribonucleic acid ("DNA") as a sequence of deoxyribonucleotides, the aforementioned interfering RNAs can also be encoded in DNA. In some embodiments, moreover, the activity or stability of these interfering RNAs may be modified by the specific binding of small molecules, proteins or other RNA molecules to them. In various embodiments, the binding may take place in vitro or within cells in vitro or in vivo, and the small molecules, proteins or other RNA molecules may arise exogenously or endogenously. Those that arise endogenously may be encoded in the cell's DNA or may arise in the course of metabolism.

The term "fluorescent activated cell sorting" or "FACS", as used herein, refers to a technique for counting, examining, and sorting microscopic particles suspended in a stream of fluid. It allows simultaneous multiparametric analysis of the physical and/or chemical characteristics of single cells flowing through an optical and/or electronic detection apparatus. Generally, a beam of light (usually laser light) of a single wavelength is directed onto a hydro-dynamically focused stream of fluid. A number of detectors are aimed at the point where the stream passes through the light beam; one in line with the light beam (Forward Scatter, correlates to cell volume) and several perpendicular to the beam, (Side Scatter, correlates to the inner complexity of the particle and/or surface roughness) and one or more fluorescent detectors. Each suspended particle passing through the beam scatters the light in some way, and fluorescent chemicals found in the particle or attached to the particle may be excited into emitting light at a lower frequency than the light source. By analyzing the combinations of scattered and fluorescent light picked up by the detectors it is then possible to derive information about the physical and chemical structure of each individual particle.

The term "data mining", as used herein, refers to the automated or convenient extraction of patterns representing knowledge implicitly stored or captured in large databases, data warehouses, internet websites, other massive information repositories, or data streams.

The terms "overexpress", "overexpressing" and grammatical equivalents, as used herein, refer to the production of a gene product at levels that exceed production in normal or control cells. The term "overexpression" or "highly expressed" may be specifically used in reference to levels of mRNA to indicate a higher level of expression than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed, the amount of 28S rRNA (an abundant RNA transcript present at essentially the same amount in all tissues) present in each sample can be used as a means of normalizing or standardizing the mRNA-specific signal observed on Northern blots. Overexpression may likewise result in elevated levels of proteins encoded by said mRNAs.

The term "apoptosis", as used herein, refers to a form of programmed cell death in multicellular organisms that involves a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation. Defective apoptotic processes have been implicated in an extensive variety of diseases; for example, defects in the apoptotic pathway have been implicated in diseases associated with uncontrolled cell proliferations, such as cancer.

The term "bioluminescence imaging" or "BLI", as used herein, refers to the noninvasive study of ongoing biological processes in living organisms (for example laboratory animals) using bioluminescence, the process of light emission in living organisms. Bioluminescence imaging utilizes native light emission from one of several organisms which bioluminescence. The three main sources are the North American firefly, the sea pansy (and related marine organisms), and bacteria like *Photorhabdus luminescens* and *Vibrio fischeri*. The DNA encoding the luminescent protein is incorporated into the laboratory animal either via a virus or by creating a transgenic animal. While the total amount of light emitted via bioluminescence is typically small and not detected by the human eye, an ultra-sensitive CCD camera can image bioluminescence from an external vantage point. Common applications of BLI include in vivo studies of infection (with bioluminescent pathogens), cancer progression (using a bioluminescent cancer cell line), and reconstitution kinetics (using bioluminescent stem cells).

The term "consensus region" or "consensus sequence", as used herein, refers to the conserved sequence motifs that show which nucleotide residues are conserved and which nucleotide residues are variable when comparing multiple DNA, RNA, or amino acid sequence alignments. When comparing the results of a multiple sequence alignment, where related sequences are compared to each other, and similar functional sequence motifs are found. The consensus sequence shows which residues are conserved (are always the same), and which residues are variable. A consensus sequence may be a short sequence of nucleotides, which is found several times in the genome and is thought to play the same role in its different locations. For example, many transcription factors recognize particular consensus sequences in the promoters of the genes they regulate. In the same way restriction enzymes usually have palindromic consensus sequences, usually corresponding to the site where they cut the DNA. Splice sites (sequences immediately surrounding the exon-intron boundaries) can also be considered as consensus sequences. In one aspect, a consensus sequence defines a putative DNA recognition site, obtained for example, by aligning all known examples of a certain recognition site and defined as the idealized sequence that represents the predominant base at each position. Related sites should not differ from the consensus sequence by more than a few substitutions.

The term "linkage", or "genetic linkage," as used herein, refers to the phenomenon that particular genetic loci of genes are inherited jointly. The "linkage strength" refers to the probability of two genetic loci being inherited jointly. As the distance between genetic loci increases, the loci are more likely to be separated during inheritance, and thus linkage strength is weaker.

The term "clonogenic assay", as used herein, refers to a technique for studying whether a given cancer therapy (for example drugs or radiation) can reduce the clonogenic survival and proliferation of tumor cells. While any type of cell may be used, human tumor cells are commonly used for oncological research. The term "clonogenic" refers to the fact that these cells are clones of one another.

The term "adjuvant therapy", as used herein, refers to additional treatment given after the primary treatment to increase the chances of a cure. In some instances, adjuvant therapy is administered after surgery where all detectable disease has been removed, but where there remains a statistical risk of relapse due to occult disease. If known disease is left behind following surgery, then further treatment is not technically "adjuvant". Adjuvant therapy may include chemotherapy, radiation therapy, hormone therapy, or biological therapy. For example, radiotherapy or chemotherapy is commonly given as adjuvant treatment after surgery for a breast cancer. Oncologists use statistical evidence to assess the risk of disease relapse before deciding on the specific adjuvant therapy. The aim of adjuvant treatment is to improve disease-specific and overall survival. Because the treatment is essentially for a risk, rather than for provable disease, it is accepted that a proportion of patients who receive adjuvant therapy will already have been cured by their primary surgery. Adjuvant chemotherapy and radiotherapy are often given following surgery for many types of cancer, including colon cancer, lung cancer, pancreatic cancer, breast cancer, prostate cancer, and some gynecological cancers.

The term "matched samples", as used herein, as for example "matched cancer samples" refers to a sample in which individual members of the sample are matched with every other sample by reference to a particular variable or quality other than the variable or quality immediately under investigation. Comparison of dissimilar groups based on specified characteristics is intended to reduce bias and the possible effects of other variables. Matching may be on an individual (matched pairs) or a group-wide basis.

The term "genomic segments", as used herein, refers to any defined part or region of a chromosome, and may contain zero, one or more genes.

The term "chemoresistant", as used herein, refers to a cancer and/or tumor that is measurably less responsive to chemotherapeutic agents than other cancers and/or tumors.

The term "co-administer", as used herein, refers to the administration of two or more agents, drugs, and/or compounds together (i.e. at the same time).

The term "diagnose" or "diagnosis", as used herein, refers to the determination, recognition, or identification of the nature, cause, or manifestation of a condition based on signs, symptoms, and/or laboratory findings.

As used herein in relation to statistical analyses discussed herein, the term "sensitivity," used interchangeably with the term "recall rate," refers to the proportion of actual positive results in a test that purports to measure (or report), above some threshold, positive and negative results. The term "specificity," used interchangeably with the term "precision," refers to the proportion of actual negative (or positive) results in a test that purports to report negative (or positive) results. A plot of sensitivity vs. (1-specificty) provides a graphical way of characterizing the test for its relative tendency to accept false positives and false negatives at various thresholds. The plot indicates the "receiver operating characteristic" (ROC) of the test.

As used herein, the term "genetic combinatorial logic" refers to a set of conditions embodied in information encoded in the genes of a cell or organism, which set of conditions comprises a system whose output of genetic information may be inferred entirely by the current inputs of genetic information to the cell or organism. Output is not at all a function of any prior state of the cell or organism.

As used herein, the term "logic circuit," also called a "logic gate," comprises a logical expression, generally a Boolean algebraic expression whose "solution," referred to as an "output," is based on particular variables called for in the expression ("inputs"). It is convenient to envision inputs as being received at "input ports." Input ports preferably detect relevant inputs discriminantly, that is, without "cross-talk" between ports, and present input without distortion to the logic evaluator. Output is determined at any instant only by the present combination of inputs to the circuit without regard to previous inputs or previous state of outputs. Such a circuit performs a specific information-processing operation assigned logically by a set of Boolean functions.

A simple logic gate is an "AND gate" that operates on two variables. If and only if the logical expression is "satisfied" by receiving both variables (at levels above the sensitivity thresholds of the input ports) does the AND gate produce an output. An AND gate consisting of two conjunctions must receive three inputs [(x AND y) AND (z)] to produce an output.

A simple "OR gate" that operates on two inputs produces an output if it receives one or the other input and also produces an output if it receives both inputs.

Hef1a:EGFP refers to a construct comprising a gene that encodes enhanced green fluorescent protein and a promoter sequence that provides a response element for the human elongation factor 1a protein.

The CCE cell line referred to herein is a type of murine embryonic stem cell line.

The 293-FT cell line, available from Invitrogen, is a derivative of a cell line that originated from a human embryonic kidney. Plasmids transfected into these cells replicate episomally.

UbC:EGFP refers to a construct comprising a gene that encodess enhanced green fluorescent protein, and a promoter sequence that provides a response element for the ubiquitin C protein.

Ahydrotetracycline ("aTc") is a derivative of the antibiotic tetracycline, which has no antibiotic activity.

DETAILED DESCRIPTION

The eradication of any cancer in a patient is an elusive goal. The resistant nature of cancerous cells continues to thwart efforts to specifically "aim" a therapeutic agent at cancer cells and definitively eliminate them from the body. Embodiments of the instant invention provide a highly selective, and largely autonomous system that is capable of detecting and destroying many cancer cell types under the control of a logic evaluator introduced into cancer cells for therapeutic purposes.

Rinaudo et al., in "A Universal RNAi-based Logic Evaluator That Operates in Mammalian Cells" Nat. Biotechnol. 25:795-801 (2007), proposed the use of short interfering RNA ("siRNA") to suppress or promote gene expression in cells by means of a stochastic control system that operates automatically on intracellular inputs. Conceptually, every ongoing process within a cell makes a "statement" about the state of the cell at any given time. To a logic evaluator, these statements are inputs susceptible to evaluation or "interpretation" as logical expressions. Depending on the evaluator's programming, a binary evaluator will find either "truth" or "not truth" in the set of inputs it interprets. Rinaudo et al. demonstrated a biological version of a logic evaluator whose output is a translation product of messenger RNA (i.e., a protein). A simple version comprised a pair of identical mRNAs and two distinct siRNAs, each of which had its own RNA interference target fused onto one member of the mRNA pair. With both species of siRNA absent from the system, protein was produced. Also, if one but not the other siRNA species was present, protein was produced. If both species were present, protein production was blocked because RNA interference was triggered against both mRNA species. Rinaudo et al. incorporated this system into cells by transfecting the cells with genes that express mRNAs bearing the siRNA binding sites. Various siRNA transfections then caused the cells to make different logic statements. Rinaudo et al. suggested that if the appearance of the siRNAs in the cells could be made to be dependent on endogenous processes ("inputs"), the system would be able to sense the inputs and logically evaluate them to yield outputs that, in turn, could be exploited to control the state of the cell.

Differential gene expression profiles, catalogued in databases, reveal for many cancer cell types gene signatures that are so different from those of healthy cells as to be reliably diagnostic of the cancer. A "gene signature" is a gene (usually, a plurality of genes) that is overexpressed or underexpressed in a cell relative to a suitable control cell. Such a gene may be referred to herein as "biomarker" of the disease in which it is differentially expressed. It may also be referred to as a "signature gene" to denote its membership in a set of genes that constitutes a signature. In some embodiments, the present invention provides a biomolecular logic circuit that selectively identifies a cancer cell by "reading" the cell's signature from molecular signals it receives as inputs at its input ports. The "reading" or output from the logic circuit then automatically triggers an apoptotic or other destructive process in that cell. In this respect, the term "biomarker" may not refer to a single gene, but to a plurality of genes, all of which the logic circuit must detect as inputs to trigger a destructive output.

In some embodiments, the system that effects the destructive process may be endogenous to the cell, but in preferred embodiments it is transferred into the cell along with the logic circuit. In preferred embodiments, the logic circuit identifies the cell from within. However, the entry means may comprise, along with the logic circuit, a means for identifying the cell from without, by binding at a binding site expressed uniquely on the surface of the target cell, for example. In various embodiments, the transfer is accomplished with a viral vector or other vector capable of transferring into the cell the genetic information necessary to the operation of the logic circuit. The vector, however, need not be capable of selecting only cancer cells for transfection, inasmuch as the transfected logic circuit, in preferred embodiments, does not actuate in cells that do not bear the signature of interest.

In one embodiment of the invention, the cell-destructive system comprises a nucleic acid that encodes an apoptotic protein. BAK and BAX are preferred, but the artisan will know of many other proteins whose expression is sufficient to cause apoptosis, so the present invention is not limited to these two apoptotic signals. The artisan can readily select any of a number of proteins encoded in commercially available nucleic acids incorporable into expression vectors by methods well-known in the art. In preferred embodiments, the nucleic acid that encodes the apoptotic signal further encodes an antisense RNA specifically complementary to a portion of the messenger RNA (preferably a portion in a non-coding region) that translates into the apoptotic protein selected for use. Thus, although the apoptotic signal may be continually transcribed, a corresponding antisense signal is also transcribed. Applicants do not wish to be bound by any theory of how embodiments of their invention work, but they believe that the transcribed antisense signal titrates away the apoptotic message by an RNA interference mechanism.

In a more preferred embodiment, the nucleic acid that encodes the aforementioned antisense transcript is engineered to further transcribe into the antisense transcript a sequence that the messenger RNA of a cancer signature gene can interact with to set up an RNA interference. The mRNA from the cancer signature gene behaves, in effect, like an antisense molecule against the antisense transcript that heretofore acted as a "governor" on apoptosis. Thus, an elevated cancer signature message erodes the antisense governor, and apoptosis proceeds apace. In preferred embodiments, the antisense transcript, although it can be interfered with by the messenger RNA of the cancer signature gene, does not have significant interference potential vis a vis the cancer signature gene. To achieve this balance, the artisan introduces specific mismatches to reduce the degree of complementarity between the two transcripts, as the art teaches (e.g., V. Patzel, Drug Discovery Today, 12:139-148, 2007).

As noted above, the gene expression signature of a cell is usually not reliably represented by a single gene. It follows that a logic circuit that responds with a cell-disabling output to an input from a single gene may not be reliable, either. Accordingly, in its most preferred embodiments, the logic circuit is constructed with input ports for two or more signature genes so that all such genes must be present and "sensed" by the logic circuit to trigger the events that result in apoptosis.

Any viral construct that can be made to reach the nucleus of a eukaryotic host cell without integrating into the genome of the cell is within the scope of the invention. As a further safeguard for normal cells that take up the logic circuit, a highly preferred embodiment of the invention comprises the use of a lentiviral vector. Lentiviruses are "RNA viruses." That is, their genomes are encoded in RNA instead of DNA. However, reverse transcriptase, an enzyme intrinsic to the virus (that is, encoded in the viral genome, not "co-opted" from the host genome), catalyzes the conversion of the RNA into DNA upon the virus's entry into a cell. Another intrinsic viral enzyme, integrase, then shuttles the DNA into the nucleus of the cell and catalyzes its integration into the cellular genome. Several well-known mutations of integrase, however, retain the shuttling function but lack the integrating function. In preferred embodiments, therefore, the logic circuit and the cell-destructive system come to reside in the cell's nucleus where its nucleic acid codes are readily transcribed, but does not enjoy the same propensity for survival that nucleic acid codes integrated into the cell's chromosomes would have. Instead, it is susceptible to degradation within the nucleus. Mutated integrases vary in the extent to which their chromosome integration function is disabled, but mutants that are most favorable in this respect are readily identified.

Persons of skill in the art know well how to select genes that the logic circuit can sense in particular cancer cell types. For example, highly expressed genes in a published and well-established gene signature for a particular cancer are preferred candidates. Note, however, that gene signatures also comprise highly underexpressed genes, generally because the cell in question is producing a repressor signal. In such cases, the repressor mRNA can serve in embodiments of the invention. Accordingly, any gene that comprises a signature for a particular cancer cell type is within the scope of the invention. Preferred genes are genes (or repressor genes) that are not highly expressed at relevant times (e.g., during a treatment period) in any healthy cells of a treated subject.

Notwithstanding the foregoing, preferred embodiments of the invention comprise logic circuit designs that respond to gene signatures rather than individual genes. Thus, in some embodiments, a logic circuit according to the invention may have an input port that "senses" a gene overexpressed in both healthy cells and diseased cells. Such a logic circuit remains within the scope of the invention if, in operation, it distinguishes between healthy and diseased cells.

Embodiments of the invention also apply to treatment of a subject over time. For example, one currently significant problem is the recurrence of breast cancer after treatment and the transformation of treatable cancer into treatment-resistant cancer. This occurs because breast cancer cells are able to change in character over time. Expression profiles of cells from the same tumor differ significantly at different stages of cancer progression. It is likely that a patient, at any given time, harbors cancer cells in several stages of cancer progression. If a therapy is effective at only one stage of cancer, the cancer will be able to recover and resume growth in a manner difficult to treat.

Thus, in some embodiments, the invention provides a method of treating a subject according to the gene signature that the subject's cancer presents at any given time or stage of disease progression. Such embodiments, moreover, need not be limited to logic circuit designs that are effective against one and only one cancer cell type at one and only one stage of disease progression. For example, a patient may present with metastatic cancer or primary tumors in multiple organs or multi-organ tumors secondary to metastasis, in which case several distinct signatures may need attention all at once. Logic circuits equipped to sense and respond to multiple gene signatures are within the scope of the invention.

EXPERIMENTAL

In response to the need for detecting cells that are slated for destruction with a high degree of discrimination, a vector transferable into cancer (and normal) cells has been designed to (1) detect within cancer cells a cancer-specific genetic message and (2) release, in response to the detection of such message, a genetic signal that translates into a cell-killing protein. Control over the production of the cell-killing protein is accomplished by means of RNA interference. The design can be viewed as a logic circuit for controlling a cell-killing system. The logic circuit is capable of identifying multiple markers of a specific cancer such that cancerous cells are destroyed selectively, leaving other cells to grow normally. The vector is further designed to deliver the logic circuit and cell-killing system in such a way that its effective lifetime in the cell is brief. The integration of three major components of the vector is demonstrated in several in vitro experiments summarized herein. All three components have been independently verified in mammalian cells [1-3] and are integrated here with a novel approach to detecting endogenous mRNA levels.

In the demonstration, genetically engineered lentiviruses infect all cells with a genetic control system analyzable as a logic circuit. Since the system, in operation, employs the phenomenon of RNA interference, it is called an RNAi logic circuit. Biomarkers in the form of messenger RNA, specific to MCF-7 breast cancer cells, are first identified. One such marker is GATA3 mRNA. GATA3 is a zinc finger protein important in tissue differentiation. To detect and respond to GATA3 mRNA, the RNAi logic circuit delivered by the engineered lentiviruses results in constitutive (or, optionally, inducible) expression of GATA3 siRNA. The lentiviral vector further comprises a killer gene (optionally under the control of an inducible promoter) fused with a special target site for the GATA3 siRNA. In cells with low endogenous levels of Gata3 mRNA, the engineered GATA3 siRNA binds and degrades killer gene mRNA (FIG. 1a). In cells with high endogenous GATA3 mRNA levels, GATA3 mRNA "uses up" or titrates away so much of the GATA3 siRNA that any remaining GATA3 siRNA is insufficient to interfere with killer gene expression, and hence cell death ensues (FIG. 1b).

It is important to recognize that using a single marker is rarely sufficient for addressing a problem as complex as cancer. To more fully address the problem, a vector is designed (in a non-limiting example) that detects the simultaneous presence of three markers specific to MCF-7 cells in a manner akin to a logic AND gate (FIG. 1c-d): Instead of equipping the vector to express a single siRNA species, the vector is designed to express (1) three species of siRNA and (2) a killer gene to which a binding site for each of the three is fused. One species is designed from TFF1. Members of the trefoil family are characterized by having at least one copy of the trefoil motif, a 40-amino acid domain that contains three conserved disulfides. They are stable secretory proteins expressed in gastrointestinal mucosa. The gene and two other related trefoil family member genes are found in a cluster on chromosome 21. The other is NPY1R, which encodes a receptor for neuropeptide Y.

To test functionality of the logic circuit in healthy cells and in cancer cells, the cells are transfected in vitro by means of a lentiviral transfer vector comprising (1) a killer gene sequence modified so that its transcription entails the insertion of an siRNA target region and (2) a nucleic acid sequence from which the corresponding siRNA is transcribed. These transiently transfected cells are then examined for changes in function, including cellular proliferation, cell cycle regulation, pro-apoptotic factor expression, and differential phosphorylation.

Cells are assayed by means of DNA microarrays, which allows a wide-scale comparison of the expression levels of multiple metabolic indicators, including genes differentially expressed during tumor progression (33, 41). Especially pertinent indicators are assayed with Q-PCR including caseins a and g (csna, csng), fatty acid bp4 (fabp4), carbonic anhydrases 3 and 6 (Car3, Car6), whey acidic protein (wap), lipoprotein lipase (lpl), zinc finger protein 503 (zfp503), adipsin (and), thyroid SPOT14 homologue (thrsp), lactalbumin a (lalba), sterol carrier protein 2 (scp2), acyl-CoA synthetase L4 (acs14), CDC-like kinase 1 (clk1), catenin D1 (ctnnd1), and tumor differential expression 1 (tde1).

The effects of the circuit on phosphorylation-dependent cellular signaling pathways are assayed using a tailored ELISA scaffold treated with whole-cell lysates (Sigma-Aldrich). Cell cycle progression and distribution throughout an experimental population is monitored with bromodeoxyuridine incorporation and DNA content assays [42]). Cellular membrane integrity is visualized by a fluorescence-enhanced cytotoxicity assay (CytoTox-ONE™, Promega, a homogeneous, fluorometric method for estimating the number of non-viable cells present in multiwell plates). Finally, proliferation rates of the four infected and uninfected cell lines are determined by cell counting.

Figure 3:
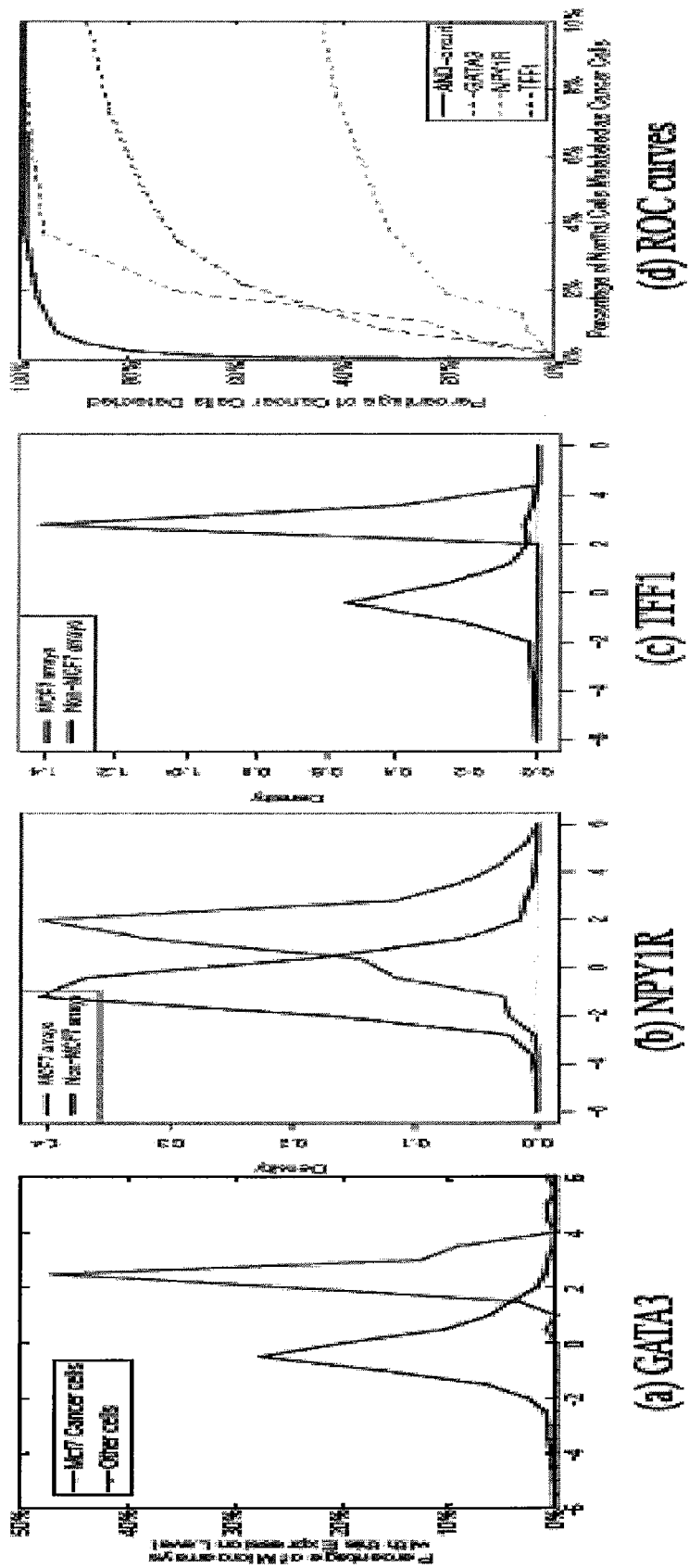
FIG. 3: (a-c) Gata3, NPYR1, and TFF1 expression levels in MCF-7 cells relative to other cells. (d) ROC curves showing the tradeoff between precision and recall. For each individual marker (dashed lines), a set of thresholds is defined where expression of that marker above a given threshold results in classification as MCF-7.

Cancer cells exhibit genetic expression profiles that deviate from their normal progenitor tissues. For example, a comparison of genetic expression profiles of various cancerous and noncancerous cell types in the 6000 cancer-related arrays in the NCBI Gene Expression Omnibus (a database repository of high throughput gene expression data and hybridization arrays, chips, and microarrays well-known to artisans), revealed 160 that are specific to MCF-7 breast adenocarcinoma cells. MCF-7 cells represent the most common type of breast cancer and have been characterized extensively in the literature [33-36]. Under normal conditions MCF-7 cells overexpress GATA3, TFF1 and NPY1R mRNA relative to healthy cells (FIG. 3a-c). The precision and recall in distinguishing MCF-7 cells using each individual marker and the combination of all three markers was compared. A tradeoff always exists between optimizing for true positives and excluding false negatives. Receiver operating characteristic (ROC) curves demonstrated this tradeoff for all cases and also showed the vast improvement obtained in both precision and recall when all three markers were used simultaneously (FIG. 3d).

Genetic combinatorial logic is not only a viable way to assess and control cell function, but is also a highly flexible technique ideally suited for the dynamic process of cancer progression. From normal to premalignant to invasive stages, the state of cancer cells (and biomarker levels expressed by those cells) evolves over time. The state of the cell at any stage implies a particular logic circuit for treatment. A logic circuit, embodied in one or more lentiviral transfer vectors, is assembled from a library of logic gates, themselves embodied in nucleic acids that encrypt genetic information. Separate lentiviral constructs are then combined into a single treatment to simultaneously treat cells in different stages of cancer.

Figure 2:
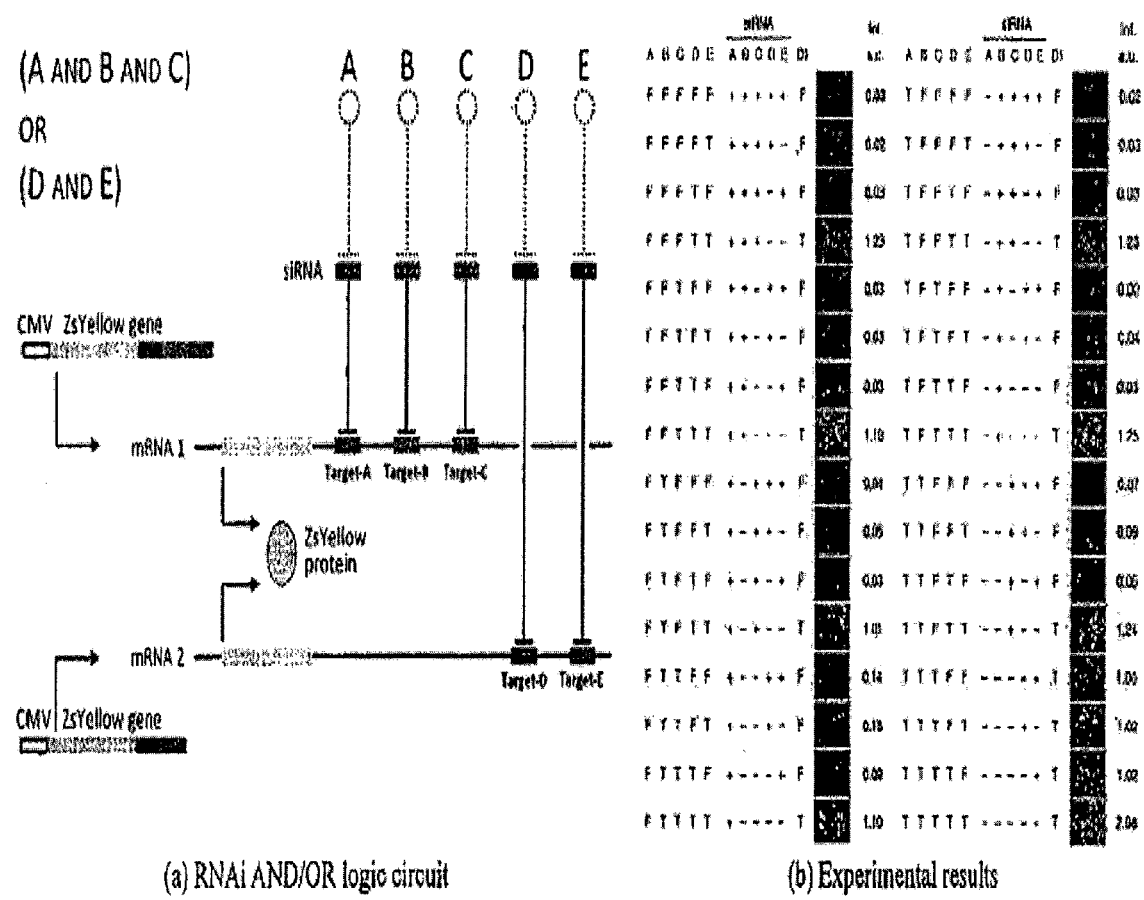
FIG. 2 An RNAi AND/OR logic circuit with five inputs [1].

An exemplary combination is represented in FIG. 2a, which depicts an RNAi logic circuit that combines two ANDs with an OR operation. The circuit comprises two output mRNA species encoding the same output protein but different noncoding regions ("different" because each has its own siRNA target sequence). The output protein will be 'on' (or 'true') as long as at least one of the two mRNA species is translated. FIG. 2b summarizes experimental results with mammalian cells "programmed" to respond (with a fluorescent signal) only when input combinations satisfy the logic function "(A AND B AND C) OR ((D AND E)." For this experiment, the presence or absence of endogenous biomarkers was simulated by directly adding siRNA as appropriate. The circuit output protein is ZsYellow. Numbers represent median FACS values for ZsYellow fluorescence.

A three-input RNAi-based AND gate as described above and specifically exemplified below reliably and selectively differentiates between cancerous and noncancerous cells and, when the AND gate is "open" (i.e., passes its signal along in the system), kills the cells in which the gate operates, while producing no significant deleterious effects in healthy cells as defined by a series of cell function assays (see above). Three candidate mRNA biomarkers found to be overexpressed in MCF-7 cells are detected by engineered siRNA interactions. Relative to the use of each individual biomarker separately, simultaneous detection of these biomarkers using an RNAi-based AND gate provides higher precision and recall for distinguishing MCF-7 cells from other cell types. This RNAi-based AND gate, combined with an apoptosis-inducing mechanism based on regulated expression of Bax and Bak proteins, eliminates MCF-7 cells within a heterogeneous cell population.

The construction of a particular logic circuit operable in MCF-7 cells first requires identifying, among phenotypically and genomically different sublines [35], the phenotype and genotype of the specific subline to be modified with the logic circuit. Using quantitative PCR (Q-PCR), total RNA extracted from MCF-7, MCF-10A, 293-FT and CCE cell lines are analyzed and GATA3, NPY1R and TFF1 mRNA levels are quantified in order to verify MCF-7 overexpression of these three biomarkers. Lentiviruses are selected for circuit delivery into the cells since they infect all cell types, both dividing and non-dividing. It is to be stressed, however, that delivery vectors other than lentiviruses or even viruses, are within the scope of the invention.

For ease of observation, an experimental RNAi circuit comprising green fluorescent protein instead of an apoptotic protein or other killer is constructed. The circuit is used to verify the functionality of such circuits in CCE cells (FIG. 4a) and in MCF7 and MCF-10A cells. Cells are infected with Hef1a-tetRKRAB-IRES2-Puro. Cells successfully infected with the construct are resistant to the antibiotic puromycin and thus may be isolated. They are then infected with PolIII$_{tetO}$:siRNAEGFP and Ubc:EGFP. To determine the efficacy of the RNAi system, the cells are grown with 1 mM anydrotetracycline ("aTc") and GFP fluorescence is quantified periodically for 72 hours using FACS. Successful repression of GFP by siRNA results in gradual reduction in fluorescence (similar to FIG. 4a).

Figure 4:
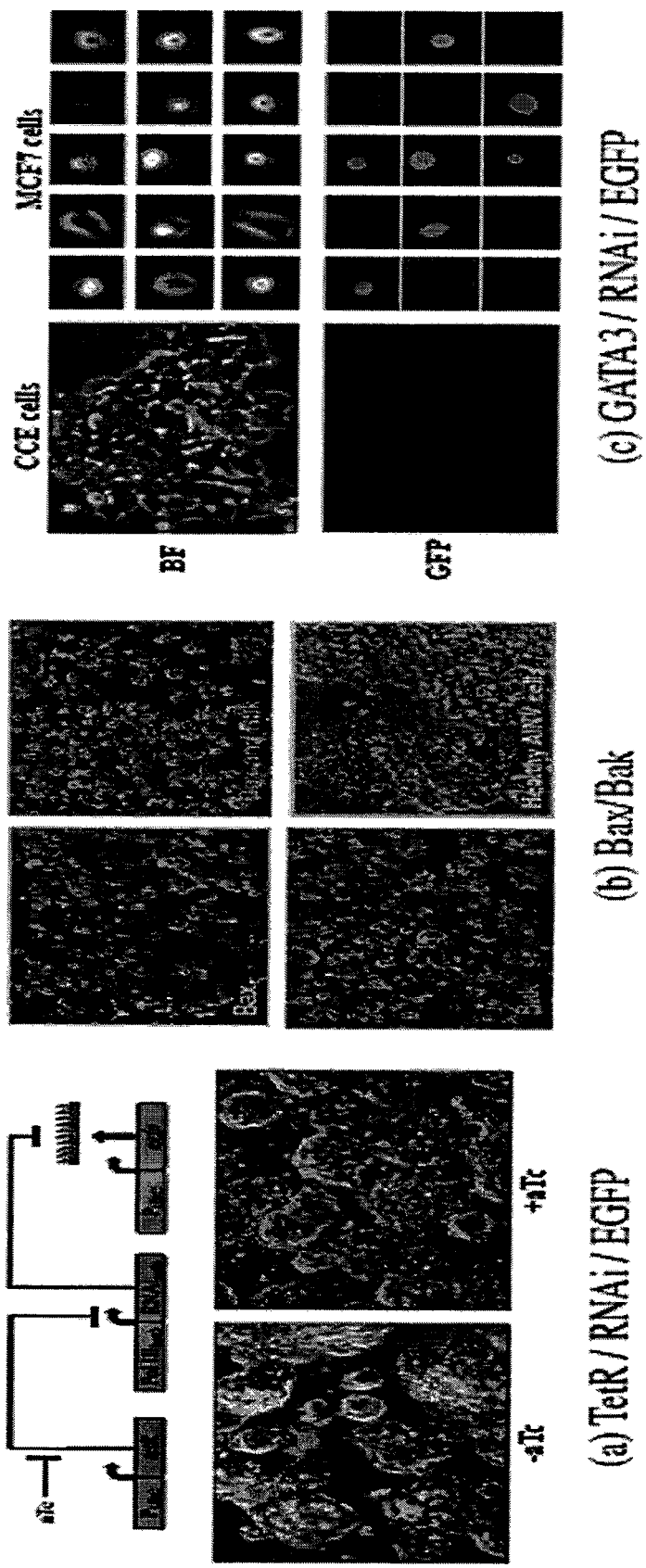
FIG. 4: (a) Preliminary results with siRNA-EGFP. CCE cells were infected with lentiviral vectors containing Hef1a:tetRKRABIRES2-Puro, PolIIItetO:siRNAEGFP, and Ubc:EGFP. Bright-field and fluorescence images taken 48 hrs post induction (_1 mM aTc) show how the RNAi construct regulates GFP expression. (b) Preliminary experimental results for TRE:Bax/Bak. Brightfield images 24 hours post-Dox induction show efficient killing based on dramatic changes in cell morphology. One day later only cell debris remained in the Bax and Bak wells. (c) Brightfield and fluorescence images were taken 72 hours post aTc induction of CCE and MCF-7 cells with the Gata3 RNAi logic circuit. EGFP replaces the killer protein. CCE cells have low Gata3 levels and thus siRNA is not titrated away resulting in no EGFP expression. MCF-7 cells have a high Gata3 levels, titrate away the siRNA, and allow EGFP expression.

Any of a wide variety of killer proteins are within the scope of the invention. Extensive literature on apoptosis suggests that overexpression of one or both of the proteins Bax and Bak is sufficient to induce apoptosis [3, 29-32]. To demonstrate that Bax and Bak are sufficient to induce apoptosis in the embodiment detailed herein, a lentivirus was constructed from two plasmids engineered to express Bax or Bak under control of Doxycycline (DOX) inducible TRE promoter. These constructs also contain ubiquitin (UbC)-driven constitutive expression of blasticidin (Bla) expression. FIG. 4b shows experimental results with AINV stem cells where DOX induction activates Bax and Bak expression, resulting in apoptosis. MCF-7 and MCF-10A cells are also infected with these constructs, selected for Bla resistance, DOX added to induce expression of Bax and Bak, and monitored for cell death over the next 48 hours. Uninduced infected cells are used as negative controls.

Apoptotic cell death is verified using the Annexin V-PE Apoptosis Detection Kit (BioVision). Each biomarker site is first verified individually by co-infecting with a corresponding PolIII:siRNA construct and a UbC:GFP fusion with the intended RNAi target site upstream or downstream of gfp. Reduction of fluorescence in cells where a given biomarker is not overexpressed indicates that siRNA for this biomarker successfully binds and silences GFP expression. For Gata3, three different shRNA sequences are used (FIG. 5). In an experiment with CCE and MCF-7 cells, Gata3mut02 siRNA expression was induced from the polIII/tetO promoter. Simultaneously, GFP mRNA fused to the target site for Gata3mut02 was transcribed constitutively from the Ubc promoter. As expected, after induction MCF-7 cells continued to fluoresce (indicating Gata3 presence and siRNA titration) whereas CCE cells did not (FIG. 4c).

Constructs that individually detect the Gata3, NFY1R and TFF1 biomarkers are made first, and then combined into one construct to implement the AND gate (FIG. 1b). As above, reduction of fluorescence indicates that siRNA successfully binds one of the target sites and silences GFP expression, in this case indicating that at least one of the biomarkers is not overexpressed. To confirm that the AND gate does not result in "high" output in cells other than MCF-7, the experiment is also conducted in MCF-10A, 293FT, and CCE cells. As the final step, the AND gate is coupled to the killing mechanism by replacing gfp with bak or bak. The full circuit within MCF-7 cells results in apoptosis, while MCF-10A, 293FT, and CCE cells remain unaffected by the circuit.

Figure 6:
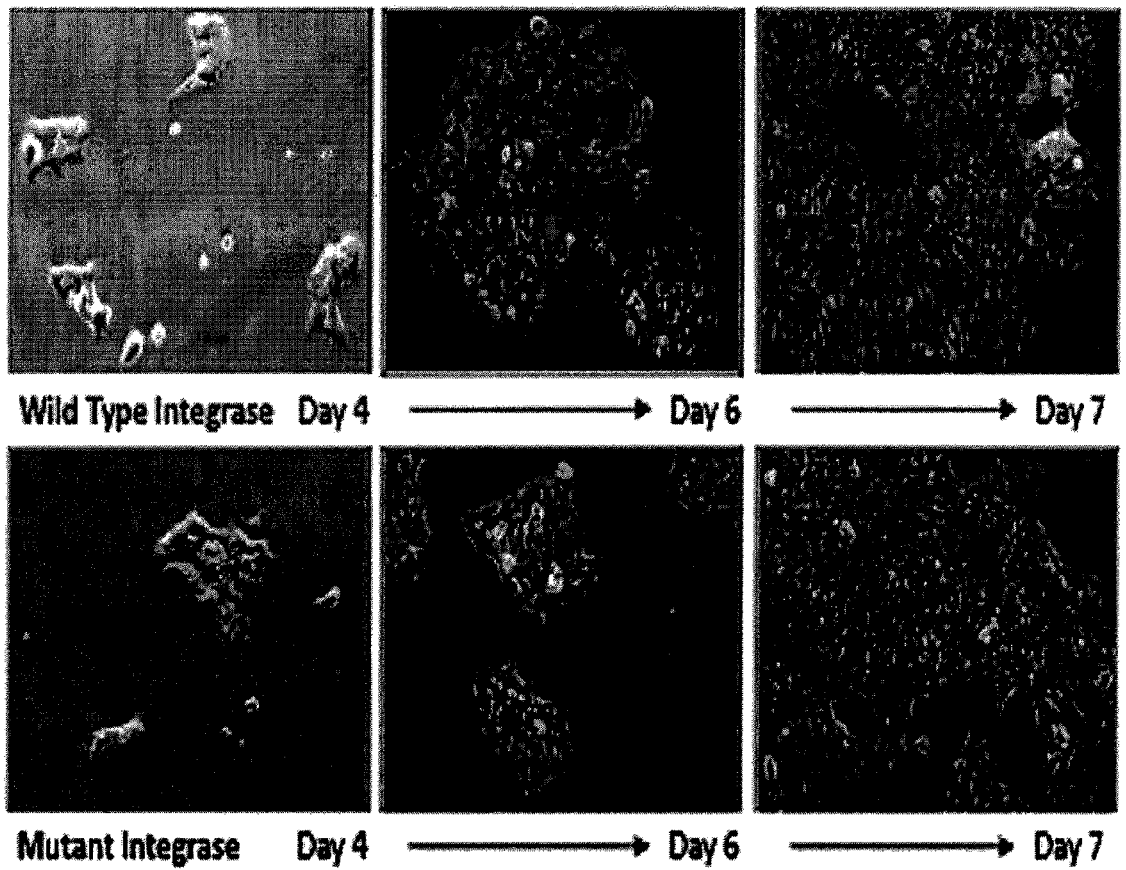
FIG. 6: Experimental results with the mutant integrase. 293FT cells are infected with the mutant integrase and Hef1a:EGFP. Four days after infection, GFP fluorescence levels are high both for the wildtype and the mutant integrase. After a week, fluorescence of cells infected with mutant integrase decreased while wild type fluorescence remained high.

To eliminate the tendency of the virus from inserting a signal into host cells that promotes cell cycling (insertional mutagenesis) while retaining the virus's ability to replicate so that it can be grown up in packaging cell lines, achieve reverse transcription after infection and express a nuclear import signal, a specific type I lentiviral mutant integrase is used. The integrase was made using a known D64V mutation of the pol gene (encoding the integrase protein) [2]. As expected, initially high GFP expression ultimately decreased in infections with Hef1a:EGFP lentivirus created with the mutant integrase, whereas wild-type integrase maintained high GFP expression throughout (FIG. 6).

The siRNA design includes specific mismatches with endogenous mRNA sequences that have been shown to essentially eliminate RNAi activity of the siRNA [38]. sequence similarity thereto. There are no such mismatches in the portion of the siRNA that targets kill messages, so the RNAi activity of the siRNA in this respect is robust. Western Blots and immunocytochemical staining for Gata3, NPY1R, and TFF1 protein and proteins with sequence similarity thereto confirm this.

REFERENCES

1. K. Rinaudo, L. Bleris, R. Maddamsetti, S. Subramanian, R. Weiss_, and Y. Benenson_. A universal rnai-based logic evaluator that operates in mammalian cells. Nature Biotechnology, 25(7), July 2007. (_co-corresponding authors).
2. A D Leavitt, G Robles, N Alesandro, and H E Varmus. Human immunodeficiency virus type 1 integrase mutants retain in vitro integrase activity yet fail to integrate viral dna efficiently during infection. J Virol, 70(2):721-728, February 1996.
3. T. Kobayashi, S. Ruan, K. Clodi, K. O. Kliche, H. Shiku, M. Andreeff, and W. Zhang. Overexpression of bax gene sensitizes k562 erythroleukemia cells to apoptosis induced by selective chemotherapeutic agents. Oncogene, 16:1587-1591, 1998.
4. R. Weiss and T. F. Knight Jr. Engineered communications for microbial robotics. In DNA6: Sixth International Workshop on DNA-Based Computers, DNA2000, pages 1-16, Leiden, The Netherlands, 2000. Springer-Verlag.
5. R. Weiss and S. Basu. The device physics of cellular logic gates. In NSC-1: The First Workshop of Non-Silicon Computing, Boston, Mass., February 2002.
6. Y. Yokobayashi, R. Weiss, and F. H. Arnold. Directed evolution of a genetic circuit. Proceedings of the National Academy of Science, 99:16587-16591, 2002.
7. S. Basu, R. Mehreja, S. Thiberge, M. Chen, and R. Weiss. Spatiotemporal control of gene expression with pulse-generating networks. Proceedings of the National Academy of Science, 101(17):6355-6360, 2004.
8. S. Hooshangi, S. Thiberge, and R. Weiss. Ultrasensitivity and noise propagation in a synthetic transcriptional cascade. Proceedings of the National Academy of Science, 102(10):3581-3586, March 2005.
9. Sara Hooshangi and Ron Weiss. The effect of negative feedback on noise propagation in transcriptional gene networks. Chaos, 16(026108), 2006.
10. R. Weiss. Challenges and opportunities in programming living cells. The Bridge, pages 39-46, 2003.
11. R. Weiss, S. Basu, A. Kalmbach, S. Hooshangi, D. Karig, R. Mehreja, and I. Netravali. Genetic circuit building blocks for cellular computation, communications, and signal processing. In Natural Computing, an International Journal, 2003.
12. R. Weiss, Hooshangi, Kambach, karig, Mehreja, and Netravali. Genetic circuit building blocks for cellular computation, communications and signal processing. Natural Computing, 2:47-84, 2003.
13. K. Basu and R. Weiss. Engineering signaling processing in cells: Towards molecular concentration band detection. Natural computing, 2:463-478, 2003.
14. Y. Yokobayashi, C. Collins, J. Leadbetter, F. Arnold, and R. Weiss. Evolutionary design of genetic circuits and cell-cell communication. Advances in Complex Systems, 6(1):37-45, 2003.
15. G. Thiberge, Jim, Sohn, and Weiss. Quantum-dot-based measurement of gene expression. 2003.
16. X. Feng, S. Hooshangi, D. Chen, G. Li, R. Weiss, and H. Rabitz. Optimizing genetic circuits by global sensitivity analysis. Biophysical Journal, in press, 2004.
17. L. You, R. Cox, R. Weiss, and F. Arnold. Programmed population control by cell-cell communication and regulated killing. Nature, 428(6985):868-871, 2004.
18. Y. Gerchman and R. Weiss. Teaching bacteria a new language. PNAS, 101:2221-2222, 2004.
19. R. Weiss and Sussman. Genetic process engineering. Cellular Computing, 2004.
20. R. Weiss. Cellular Computation and Communications using Engineered Genetic Regulatory Networks. PhD thesis, Massachusetts Institute of Technology, September 2001.
21. R. Weiss, G. Homsy, and T. F. Knight Jr. Toward in-vivo digital circuits. In Dimacs Workshop on Evolution as Computation, Princeton, N.J., January 1999.
22. S. Basu, Y. Gerchman, C. H. Collins, F. H. Arnold, and R. Weiss. A synthetic multicellular system for programmed pattern formation. Nature, 434(7037):1130-1134, 2005.
23. V. Hsu, Fomundam, Gerchman, Basu, Karig, Hooshangi, and Weiss. Dynamic control in a coordinated multi-cellular maze solving system. American Controls Conference, 2005.
24. D. Karig and R. Weiss. Signal-amplifying genetic circuit enables in vivo observation of weak promoter activation in the rhl quorum sensing system. Biotechnol Bioeng., 89(6):709-718, 2005.
25. D. Braun, S. Basu, and R. Weiss. Parameter estimation for two synthetic gene networks: A case study. ICASSP, pages V769-V772, March 2005.
26. R. McDaniel and R. Weiss. Advances in synthetic biology: on the path from prototypes to applications. Curr Opin Biotechnol, 16:476-483, 2005.
27. M. Chen and R. Weiss. Artificial cell-cell communication in *saccharomyces cerevisiae* using signaling elements from *Arabidopsis thaliana*. Nature Biotech, in press, 2005.
28. K. Brenner, D. Karig, R. Weiss_, and F. Arnold_. Engineered bidirectional communication mediates a consensus in a microbial biofilm consurtium. Proceedings of the National Academy of Science, 104(44), October 2007. (_co-corresponding authors).
29. X. Saelens, N. Festjens, L. Vande Walle, M. van Gurp, G. van Loo, and P. Vandenabeele. Toxic proteins released from mitochondria in cell death. Oncogene, 23:2861-2874, 2004.
30. J. P. Upton, A. J. Valentijn, L. Zhang, and A. P. Gilmore. The n-terminal conformation of bax regulates cell commitment to apoptosis. Cell Death Differ, 14:932-942, 2007.
31. J. C. Goldstein, N. J. Waterhouse, J. Juin, G. I. Evan, and D. R. Green. The coordinate release of cytochrome c during apoptosis is rapid, complete and kinetically invariant. Nat Cell Biol, 2:156-162, 2000.
32. D. A. Kubli, J. E. Ycaza, and A. B. Gustafsson. Bnip3 mediates mitochondrial dysfunction and cell death through bax and bak. Biochem J, 405:407-415, 2007.
33. H. Kouros-Mehr, S K Bechis, E M Slorach, L E Littlepage, M Egeblad, A J Ewald, S Y Pai, I C Ho, and Z Werb. Gata-3 links tumor differentiation and dissemination in a luminal breast cancer model. Cancer Cell, 13(2):141-152, February 2008.
34. M. Dejori and M. Stetter. Identifying interventional and pathogenic mechanisms by generative inverse modeling of gene expression profiles. Journal of Computational Biology, 11(6):1135-1148, 2004.
35. M Nugoli, P Chuchana, J Vendrell, B Orsetti, L Ursule, C Nguyen, D Birnbaum, E J Douzery, P Cohen, and C Theillet. Genetic variability in mcf-7 sublines: evidence of rapid genomic and rna expression profile modifications. BMC Cancer, 3(13), April 2003.
36. M. Wiznerowicz and D. Trono. Conditional suppression of cellular genes: Lentivirus vector-mediated drug-inducible rna interference. Journal of Virology, 77(16):8957-8961, August 2003.
37. K. Ui-Tei, Y. Naito, F. Takahashi, T. Haraguchi, H. Ohki-Hamazaki, A. Juni, R. Ueda, and K. Saigo. Guidelines for the selection of highly effective sirna sequences for mammalian and chick rna interference. Nucleic Acids Res, 32:936-948, 2004.
38. V. Patzel. In silico selection of active sirna. Drug Discovery Today, 12:139-148, 2007.
39. S Griffiths-Jones. The microrna registry. Nuc. Acid Research, 32:D109-D111, 2004.
40. M Germain, J Milburn, and V Duronio. Mcl-1 inhibits bax in the absence of mcl-1/bax interaction. The Journal of Biological Chemistry, 283(10):6384-6392, 2007.
41. M C Abba, J A Drake, K A Hawkins, Y Hu, H Sun, C Notcovich, S Gaddis, A Sahin, K Baggerly, and C M Aldaz. Transcriptomic changes in human breast cancer progression as determined by serial analysis of gene expression. Breast Cancer Research, 6(1):499-513, July 2004.
42. H. A. Coller, L. Sang, and J. M. Roberts. A new description of cellular quiescence. PLoS Biol, 4:1-21, 2006.
43. A. G. Lloyd, Y. S. Ng, M. A. Muesing, V. Simon, and L. C. F. Mulder. Characterization of hiv-1 integrase n-terminal mutant viruses. Virology, 360:129-135, 2007.
44. S. Philippe, C. Sarkis, M. Barkats, H. Mammeri, C. Ladroue, C. Petit, J. Mallet, and C. Serguera. Lentiviral vectors with a defective integrase allow efficient and sustained transgene expression in vitro and in vivo. Proc. Natl. Acad. Sci., 103:17684-17689, 2006.
45. R. J. Yanez-Munoz, K. S., Balaggan, A. MacNeil, S. J. Howe, M. Schmidt, A. J. Smith, P. Buch, R. E. MacLaren, P. N. Anderson, S. E. Barker, Y. Duran, C. Bartholomae, C. vonKalle, J. R. Heckenlively, C. Kinnon, R. R. Ali, and A. J. Thrasher. Effective gene therapy with nonintegrating lentiviral vectors. Nature Medicine, 12:348-353, 2006.
46. R. dos Santos Coura and N. B. Nardi. The state of the art of adeno-associated virus-based vectors in gene therapy. Virology Journal, 4:1-7, 2007.
47. K. Park, W. J. Kim, Y. H. Cho, Y. I. Lee, H. Lee, S. Jeong, E. S. Cho, S. I. Chang, S. K. Moon, B. S. Kang, Y. J. Kim, and S. H. Cho. Cancer gene therapy using adeno-associated vectors. Frontiers in Bioscience, 13:2653-2659, 2008.

The invention claimed is:
1. A composition comprising a vector for transfecting a cell, the vector comprising:
 a) a first nucleic acid sequence encoding an antisense agent, said antisense agent comprising a first RNA interference target for a transcript of a gene endogenous to the cell, and
 b) a second nucleic acid sequence comprising
  i) a third nucleic acid sequence encoding a cell-killing agent, and
  ii) a fourth nucleic acid sequence comprising a second RNA interference target that is substantially complementary to said first RNA interference target,
wherein said third nucleic acid sequence is fused to said fourth nucleic acid sequence, and wherein said antisense agent does not alter protein translation by said second RNA interference target, and wherein

1) said first RNA interference target is selected from the group consisting of GATA3 antisense sequences CGAGTCGCTGAAGAGGTTCTG (SEQ ID NO:1), CGAGTCGCTGAAGAGGTTCTGCUUCAAGA-GAGCAGAACCTCTTCAGC GACTCG (SEQ ID NO:3), GTAAGTGGTATAATTGTCTGG (SEQ ID NO:6), and
 GTAAGTGGTATAATTGTCTGGCUUCAAGA-GAGCCAGACAATTATACCA CTTAC (SEQ ID NO:8),
2) said cell-killing agent is selected from the group consisting of BAK protein and BAX protein, and
3) said second RNA interference target is selected from the group consisting of GATA3 mRNA sequences CAGAACCTCTTCAGCGACTCG (SEQ ID NO:5) and CCAGACAATTATACCACTTAC (SEQ ID NO:10).

2. A composition comprising a vector for transfecting a cell, the vector comprising:
  a) a first nucleic acid sequence encoding an antisense agent, said antisense agent comprising a first RNA interference target for a transcript of a gene that is endogenous to the cell and that is a biomarker for disease, and
  b) a second nucleic acid sequence comprising
    i) a third nucleic acid sequence encoding a cell-killing agent, and
    ii) a fourth nucleic acid sequence comprising a second RNA interference target that is substantially complementary to said first RNA interference target,
  wherein said third nucleic acid sequence is fused to said fourth nucleic acid sequence, wherein, in the presence of said biomarker, said third nucleic acid sequence and said fourth nucleic acid sequence are expressed, and wherein, in the absence of said biomarker, binding of said second RNA interference target to said second RNA interference target inhibits expression of said cell-killing agent, and wherein said antisense agent does not alter protein translation by said second RNA interference target, and wherein
  1) said first RNA interference target is selected from the group consisting of GATA3 antisense sequences CGAGTCGCTGAAGAGGTTCTG (SEQ ID NO:1), CGAGTCGCTGAAGAGGTTCTGCUUCAAGA-GAGCAGAACCTCTTCAGC GACTCG (SEQ ID NO:3), GTAAGTGGTATAATTGTCTGG (SEQ ID NO:6), and
  GTAAGTGGTATAATTGTCTGGCUUCAAGA-GAGCCAGACAATTATACCA CTTAC (SEQ ID NO:8),
  2) said cell-killing agent is selected from the group consisting of BAK protein and BAX protein, and
  3) said second RNA interference target is selected from the group consisting of GATA3 mRNA sequences CAGAACCTCTTCAGCGACTCG (SEQ ID NO:5) and CCAGACAATTATACCACTTAC (SEQ ID NO:10).

* * * * *

```
SEQUENCE LISTING

<160> NUMBER OF SEQ ID NOS: 15

<210> SEQ ID NO 1
<211> LENGTH: 21
<212> TYPE: DNA
<213> ORGANISM: Artificial sequence
<220> FEATURE:
<223> OTHER INFORMATION: Synthetic

<400> SEQUENCE: 1
cgagtcgctg aagaggttct g                                                   21

<210> SEQ ID NO 2
<211> LENGTH: 21
<212> TYPE: DNA
<213> ORGANISM: Artificial sequence
<220> FEATURE:
<223> OTHER INFORMATION: Synthetic

<400> SEQUENCE: 2
cagaacctct tccccgactc t                                                   21

<210> SEQ ID NO 3
<211> LENGTH: 53
<212> TYPE: DNA
<213> ORGANISM: Artificial sequence
<220> FEATURE:
<223> OTHER INFORMATION: Synthetic

<400> SEQUENCE: 3
cgagtcgctg aagaggttct gcuucaagag agcagaacct cttcagcgac tcg               53

<210> SEQ ID NO 4
<211> LENGTH: 21
<212> TYPE: DNA
<213> ORGANISM: Artificial sequence
<220> FEATURE:
```

<223> OTHER INFORMATION: Synthetic

<400> SEQUENCE: 4
cgagtcgctg aagaggttct g                                              21

<210> SEQ ID NO 5
<211> LENGTH: 21
<212> TYPE: DNA
<213> ORGANISM: Artificial sequence
<220> FEATURE:
<223> OTHER INFORMATION: Synthetic

<400> SEQUENCE: 5
cagaacctct tcagcgactc g                                              21

<210> SEQ ID NO 6
<211> LENGTH: 21
<212> TYPE: DNA
<213> ORGANISM: Artificial sequence
<220> FEATURE:
<223> OTHER INFORMATION: Synthetic

<400> SEQUENCE: 6
gtaagtggta taattgtctg g                                              21

<210> SEQ ID NO 7
<211> LENGTH: 21
<212> TYPE: DNA
<213> ORGANISM: Artificial sequence
<220> FEATURE:
<223> OTHER INFORMATION: Synthetic

<400> SEQUENCE: 7
ccagacaatt ataacacttc g                                              21

<210> SEQ ID NO 8
<211> LENGTH: 53
<212> TYPE: DNA
<213> ORGANISM: Artificial sequence
<220> FEATURE:
<223> OTHER INFORMATION: Synthetic

<400> SEQUENCE: 8
gtaagtggta taattgtctg gcuucaagag agccagacaa ttataccact tac           53

<210> SEQ ID NO 9
<211> LENGTH: 21
<212> TYPE: DNA
<213> ORGANISM: Artificial sequence
<220> FEATURE:
<223> OTHER INFORMATION: Synthetic

<400> SEQUENCE: 9
gtaagtggta taattgtctg g                                              21

<210> SEQ ID NO 10
<211> LENGTH: 21
<212> TYPE: DNA
<213> ORGANISM: Artificial sequence
<220> FEATURE:
<223> OTHER INFORMATION: Synthetic

<400> SEQUENCE: 10
ccagacaatt ataccactta c                                              21

```
<210> SEQ ID NO 11
<211> LENGTH: 23
<212> TYPE: DNA
<213> ORGANISM: Artificial sequence
<220> FEATURE:
<223> OTHER INFORMATION: Synthetic

<400> SEQUENCE: 11
ugcgcguccg gucucgggc ccg                                      23

<210> SEQ ID NO 12
<211> LENGTH: 23
<212> TYPE: DNA
<213> ORGANISM: Artificial sequence
<220> FEATURE:
<223> OTHER INFORMATION: Synthetic

<400> SEQUENCE: 12 cgguccagc gacgggacgu gcg                                      23

<210> SEQ ID NO 13
<211> LENGTH: 55
<212> TYPE: DNA
<213> ORGANISM: Artificial sequence
<220> FEATURE:
<223> OTHER INFORMATION: Synthetic

<400> SEQUENCE: 13
acgcgcaggc cagagaccca ggcuucaaga gagccugggu cucuggccug cgcgu    55

<210> SEQ ID NO 14
<211> LENGTH: 23
<212> TYPE: DNA
<213> ORGANISM: Artificial sequence
<220> FEATURE:
<223> OTHER INFORMATION: Synthetic

<400> SEQUENCE: 14
ugcgcguccg gucucggu ccg                                       23

<210> SEQ ID NO 15
<211> LENGTH: 23
<212> TYPE: DNA
<213> ORGANISM: Artificial sequence
<220> FEATURE:
<223> OTHER INFORMATION: Synthetic

<400> SEQUENCE: 15 cggaccaga gaccggacgc gca                                      23
```